United States Patent [19]

Fiers et al.

[11] Patent Number: 5,422,104
[45] Date of Patent: Jun. 6, 1995

[54] TNF-MUTEINS

[75] Inventors: Walter Fiers, Destelbergen; Jan Tavernier, Balegem; Xaveer Van Ostade, Antwerp, all of Belgium

[73] Assignee: Hoffmann-La Roche Inc., Nutley, N.J.

[21] Appl. No.: 794,400

[22] Filed: Nov. 20, 1991

[30] Foreign Application Priority Data

Nov. 21, 1990 [EP]  European Pat. Off. ........... 90810901

[51] Int. Cl.⁶ ................... A61K 45/05; C07K 13/00; C12P 21/06
[52] U.S. Cl. ................... 424/85.1; 530/351; 435/69.5
[58] Field of Search ............... 530/351, 395, 402; 430/144; 435/69.5; 424/85.1; 574/2.8

[56] References Cited

U.S. PATENT DOCUMENTS

| 4,650,674 | 3/1987 | Aggarwal et al. | |
| 4,948,875 | 8/1990 | Tanaka et al. | 530/350 |
| 4,990,455 | 2/1991 | Yamagishi et al. | 435/69.5 |

FOREIGN PATENT DOCUMENTS

| 40162 | 12/1989 | Australia. |
| 0168214 | 1/1986 | European Pat. Off.. |
| 3843534 | 7/1990 | Germany. |
| 88/06625 | 9/1988 | WIPO. |

OTHER PUBLICATIONS

Yamagishi et al, *Protein Eng.* 3(4), 1990 p. 372 (abst only).
Wells et al, *Science* 243, 1989, pp. 1330–1336.
Goh et al, *Protein Eng.* 4(7) 1991, pp. 785–791.
Carlino et al, *JBC* 262, 1987, pp. 958–961.
Tavernier et al, *J. Mol. Biol* 211(2) 1990, pp. 493–502.
Eck et al, *JBC* 264, 1989, pp. 17595–17606.
Yamagishi et al Protein Engineering 3(8) 1990, pp. 713–719.
Yamagishi et al Protein Engineering 3(4) 1990 (previously cited).
Tsujimoto et al, J. Biochem 101, 1987, pp. 919–925.
Tartaglia, et al, Immunology Today, vol. 13, No. 5, (1992).
Barrett, et al, Eur. Journal Immunology vol. 21, 1649–1656 (1991).
Lewis, et al, Proc. Natl. Acad. Science vol. 88, 2830–2834 (1991).
Masegi, et al. Protein Engineering Engineering 375–376 (1889).
Tsukio, Patent Abstract of Japan, vol. 13, No. 119 (1989).
Ostade, et al. The Embo Journal, vol. 10, No. 4 827–836 (1991).

*Primary Examiner*—Garnette D. Draper
*Assistant Examiner*—K. Cochrane Carlson
*Attorney, Agent, or Firm*—George M. Gould; William H. Epstein; Catherine A. Picut

[57] ABSTRACT

It is an object of this invention to provide a human Tumor Necrosis Factor mutein or a pharmaceutically acceptable salt thereof characterized in that the TNF sequence is changed by a deletion, insertion, substitution or combinations thereof, of one or more amino acids so that the mutein shows a significant difference between its binding affinity to the human p75-Tumor-Necrosis-Factor-Receptor and to the human p55-Tumor-Necrosis-Factor-Receptor. The invention also includes DNA sequences coding for such muteins, vectors comprising such DNA sequences, host cells transformed with such vectors and a process for the production of such muteins employing such transformed host cells and pharmaceutical compositions containing such muteins and their use for the treatment of illnesses, for example cancer.

4 Claims, 16 Drawing Sheets

```
         HindIII
   1 AAGCTTCACG CTGCCGCAAG CACTCAGGGC GCAAGGGCTG CTAAAGGAAG
  51 CGGAACACGT AGAAAGCCAG TCCGCAGAAA CGGTGCTGAC CCCGGATGAA
 101 TGTCAGCTAC TGGGCTATCT GGACAAGGGA AAACGCAAGC GCAAAGAGAA
 151 AGCAGGTAGC TTGCAGTGGG CTTACATGGC GATAGCTAGA CTGGGCGGTT
 201 TTATGGACAG CAAGCGAACC GGAATTGCCA GCTGGGGCGC CCTCTGGTAA
 251 GGTTGGGAAG CCCTGCAAAG TAAACTGGAT GGCTTTCTTG CCGCCAAGGA
 301 TCTGATGGCG CAGGGGATCA AGATCTGATC AAGAGACAGG ATGACGGTCG
 351 TTTCGCATGC TTGAACAAGA TGGATTGCAC GCAGGTTCTC CGGCCGCTTG
 401 GGTGGAGAGG CTATTCGGCT ATGACTGGGC ACAACAGACA ATCGGCTGCT
 451 CTGATGCCGC CGTGTTCCGG CTGTCAGCGC AGGGGCGCCC GGTTCTTTTT
 501 GTCAAGACCG ACCTGTCCGG TGCCCTGAAT GAACTGCAGG ACGAGGCAGC
 551 GCGGCTATCG TGGCTGGCCA CGACGGGCGT TCCTTGCGCA GCTGTGCTCG
 601 ACGTTGTCAC TGAAGCGGGA AGGGACTGGC TGCTATTGGG CGAAGTGCCG
 651 GGGCAGGATC TCCTGTCATC TCACCTTGCT CCTGCCGAGA AAGTATCCAT
 701 CATGGCTGAT GCAATGCGGC GGCTGCATAC GCTTGATCCG GCTACCTGCC
 751 CATTCGACCA CCAAGCGAAA CATCGCATCG AGCGAGCACG TACTCGGATG
 801 GAAGCCGGTC TTGTCGATCA GGATGATCTG GACGAAGAGC ATCAGGGGCT
 851 CGCGCCAGCC GAACTGTTCG CCAGGCTCAA GGCGCGCATG CCCGACGGCG
 901 AGGATCTCGT CGTGACCCAT GGCGATGCCT GCTTGCCGAA TATCATGGTG
 951 GAAAATGGCC GCTTTTCTGG ATTCATCGAC TGTGGCCGGC TGGGTGTGGC
1001 GGACCGCTAT CAGGACATAG CGTTGGCTAC CCGTGATATT GCTGAAGAGC
1051 TTGGCGGCGA ATGGGCTGAC CGCTTCCTCG TGCTTTACGG TATCGCCGCT
1101 CCCGATTCGC AGCGCATCGC CTTCTATCGC CTTCTTGACG AGTTCTTCTG
1151 AGCGGGACTC TGGGGTTCGA AATGACCGAC CAAGCGACGC CCAACCTGCC
1201 ATCACGAGAT TTCGATTCCA CCGCCGCCTT CTATGAAAGG TTGGGCTTCG
1251 GAATCGTTTT CCGGGACGCC GGCTGGATGA TCCTCCAGCG CGGGGATCTC
1301 ATGCTGGAGT TCTTCGCCCA CCCCGGGCTC GATCCCCTCG CGAGTTGGTT
```

FIG. 2b

1351 CAGCTGCTGC CTGAGGCTGG ACGACCTCGC GGAGTTCTAC CGGCAGTGCA

1401 AATCCGTCGG CATCCAGGAA ACCAGCAGCG GCTATCCGCG CATCCATGCC

1451 CCCGAACTGC AGGAGTGGGG AGGCACGATG GCCGCTTTGG TCGACAATTC  [SalI over GTCGAC]

1501 GCGCTAACTT ACATTAATTG CGTTGCGCTC ACTGCCCGCT TTCCAGTCGG

1551 GAAACCTGTC GTGCCAGCTG CATTAATGAA TCGGCCAACG CGCGGGGAGA

1601 GGCGGTTTGC GTATTGGGCG CCAGGGTGGT TTTTCTTTTC ACCAGTGAGA

1651 CGGGCAACAG CTGATTGCCC TTCACCGCCT GGCCCTGAGA GAGTTGCAGC

1701 AAGCGGTCCA CGCTGGTTTG CCCCAGCAGG CGAAAATCCT GTTTGATGGT

1751 GGTTAACGGC GGGATATAAC ATGAGCTGTC TTCGGTATCG TCGTATCCCA

1801 CTACCGAGAT ATCCGCACCA ACGCGCAGCC CGGACTCGGT AATGGCGCGC

1851 ATTGCGCCCA GCGCCATCTG ATCGTTGGCA ACCAGCATCG CAGTGGGAAC

1901 GATGCCCTCA TTCAGCATTT GCATGGTTTG TTGAAAACCG GACATGGCAC

1951 TCCAGTCGCC TTCCCGTTCC GCTATCGGCT GAATTTGATT GCGAGTGAGA

2001 TATTTATGCC AGCCAGCCAG ACGCAGACGC GCCGAGACAG AACTTAATGG

2051 GCCCGCTAAC AGCGCGATTT GCTGGTGACC CAATGCGACC AGATGCTCCA

2101 CGCCCAGTCG CGTACCGTCT TCATGGGAGA AAATAATACT GGTGATGGGT

2151 GTCTGGTCAG AGACATCAAG AAATAACGCC GGAACATTAG TGCAGGCAGC

2201 TTCCACAGCA ATGGCATCCT GGTCATCCAG CGGATAGTTA ATGATCAGCC

2251 CACTGACGCG TTGCGCGAGA AGATTGTGCA CCGCCGCTTT ACAGGCTTCG

2301 ACGCCGCTTC GTTCTACCAT CGACACCACC ACGCTGGCAC CCAGTTGATC

2351 GGCGCGAGAT TTAATCGCCG CGACAATTTG CGACGGCGCG TGCAGGGCCA

2401 GACTGGAGGT GGCAACGCCA ATCAGCAACG ACTGTTTGCC CGCCAGTTGT

2451 TGTGCCACGC GGTTGGGAAT GTAATTCAGC TCCGCCATCG CCGCTTCCAC

2501 TTTTTCCCGC GTTTTCGCAG AAACGTGGCT GGCCTGGTTC ACCACGCGGG

2551 AAACGGTCTG ATAAGAGACA CCGGCATACT CTGCGACATC GTATAACGTT

2601 ACTGGTTTCA CATTCACCAC CCTGAATTGA CTCTCTTCCG GGCGCTATCA

2651 TGCCATACCG CGAAAGGTTT TGCGCCATTC GATGGTGTCA ACGTAAATGC  [SalI under TGCGCCATTC GATGGTGTCA]

2701 ATGCCGCTTC GCCTTCGCGC GCGAATTGTC GACCCTGTCC CTCCTGTTCA

FIG. 2c

```
2751 GCTACTGACG GGGTGGTGCG TAACGGCAAA AGCACCGCCG GACATCAGCG
2801 CTAGCGGAGT GTATACTGGC TTACTATGTT GGCACTGATG AGGGTGTCAG
2851 TGAAGTGCTT CATGTGGCAG GAGAAAAAAG GCTGCACCGG TGCGTCAGCA
2901 GAATATGTGA TACAGGATAT ATTCCGCTTC CTCGCTCACT GACTCGCTAC
2951 GCTCGGTCGT TCGACTGCGG CGAGCGGAAA TGGCTTACGA ACGGGCGGA
3001 GATTTCCTGG AAGATGCCAG GAAGATACTT AACAGGGAAG TGAGAGGGCC
3051 GCGGCAAAGC CGTTTTCCA TAGGCTCCGC CCCCCTGACA AGCATCACGA
3101 AATCTGACGC TCAAATCAGT GGTGGCGAAA CCCGACAGGA CTATAAAGAT
3151 ACCAGGCGTT TCCCCTGGCG GCTCCCTCGT GCGCTCTCCT GTTCCTGCCT
3201 TTCGGTTTAC CGGTGTCATT CCGCTGTTAT GGCCGCGTTT GTCTCATTCC
3251 ACGCCTGACA CTCAGTTCCG GGTAGGCAGT TCGCTCCAAG CTGGACTGTA
3301 TGCACGAACC CCCCGTTCAG TCCGACCGCT GCGCCTTATC CGGTAACTAT
3351 CGTCTTGAGT CCAACCCGGA AAGACATGCA AAAGCACCAC TGGCAGCAGC
3401 CACTGGTAAT TGATTTAGAG GAGTTAGTCT TGAAGTCATG CGCCGGTTAA
3451 GGCTAAACTG AAAGGACAAG TTTTGGTGAC TGCGCTCCTC CAAGCCAGTT
3501 ACCTCGGTTC AAAGAGTTGG TAGCTCAGAG AACCTTCGAA AAACCGCCCT
3551 GCAAGGCGGT TTTTTCGTTT TCAGAGCAAG AGATTACGCG CAGACCAAAA
3601 CGATCTCAAG AAGATCATCT TATTAATCAG ATAAAATATT TCTAGATTTC
3651 AGTGCAATTT ATCTCTTCAA ATGTAGCACC TGAAGTCAGC CCCATACGAT
3701 ATAAGTTGTT AATTCTCATG TTTGACAGCT TATCATCGAT
```

FIG. 2d

```
          XhoI
    1 CTCGAGAAAT CATAAAAAAT TTATTTGCTT TGTGAGCGGA TAACAATTAT
                                                EcoRI
   51 AATAGATTCA ATTGTGAGCG GATAACAATT TCACACAGAA TTCATTAAAG
  101 AGGAGAAATT AAGCATGGTC AGATCATCTT CTCGAACCCC GAGTGACAAG
  151 CCTGTAGCCC ATGTTGTCGC GAACCCTCAA GCTGAGGGGC AGCTCCAGTG
  201 GCTGAACCGC CGGGCCAATG CCCTCCTGGC CAATGGCGTG GAGCTGAGAG
  251 ATAACCAGCT GGTGGTGCCA TCAGAGGGCC TGTACCTCAT CTACTCCCAG
  301 GTCCTCTTCA AGGGCCAAGG CTGCCCCTCC ACCCATGTGC TCCTCACCCA
  351 CACCATCAGC CGCATCGCCG TCTCCTACCA GACCAAGGTC AACCTCCTCT
  401 CTGCCATCAA GAGCCCCTGC CAGAGGGAGA CCCCAGAGGG GGCTGAGGCC
  451 AAGCCCTGGT ATGAGCCCAT CTATCTGGGA GGGGTCTTCC AGCTGGAGAA
  501 GGGTGACCGA CTCAGCGCTG AGATCAATCG GCCCGACTAT CTCGACTTTG
  551 CCGAGTCTGG GCAGGTCTAC TTTGGGATCA TTGCCCTGTG AGGAGGACGA
  601 ACATCCAACC TTCCCAAACG CCTCCCCTGC CCCAATCCCT TTATTACCCC
  651 CTCCTTCAGA CACCCTCAAC CTCTTCTGGC TCAAAAAGAG AATTGGGGGC
                   HindIII
  701 TTAGGGTCGG AACCCAAGCT TGGACTCCTG TTGATAGATC CAGTAATGAC
  751 CTCAGAACTC CATCTGGATT TGTTCAGAAC GCTCGGTTGC CGCCGGGCGT
  801 TTTTTATTGG TGAGAATCCA AGCTAGCTTG GCGAGATTTT CAGGAGCTAA
  851 GGAAGCTAAA ATGGAGAAAA AAATCACTGG ATATACCACC GTTGATATAT
  901 CCCAATGGCA TCGTAAAGAA CATTTTGAGG CATTTCAGTC AGTTGCTCAA
  951 TGTACCTATA ACCAGACCGT TCAGCTGGAT ATTACGGCCT TTTTAAAGAC
 1001 CGTAAAGAAA AATAAGCACA AGTTTTATCC GGCCTTTATT CACATTCTTG
 1051 CCCGCCTGAT GAATGCTCAT CCGGAATTTC GTATGGCAAT GAAAGACGGT
 1101 GAGCTGGTGA TATGGGATAG TGTTCACCCT TGTTACACCG TTTTCCATGA
 1151 GCAAACTGAA ACGTTTTCAT CGCTCTGGAG TGAATACCAC GACGATTTCC
 1201 GGCAGTTTCT ACACATATAT TCGCAAGATG TGGCGTGTTA CGGTGAAAAC
 1251 CTGGCCTATT TCCCTAAAGG GTTTATTGAG AATATGTTTT TCGTCTCAGC
```

FIG. 3b

```
1301 CAATCCCTGG GTGAGTTTCA CCAGTTTTGA TTTAAACGTG GCCAATATGG

1351 ACAACTTCTT CGCCCCCGTT TTCACCATGG GCAAATATTA TACGCAAGGC

1401 GACAAGGTGC TGATGCCGCT GGCGATTCAG GTTCATCATG CCGTCTGTGA

1451 TGGCTTCCAT GTCGGCAGAA TGCTTAATGA ATTACAACAG TACTGCGATG

1501 AGTGGCAGGG CGGGGCGTAA TTTTTTTAAG GCAGTTATTG GTGCCCTTAA

1551 ACGCCTGGGG TAATGACTCT CTAGCTTGAG GCATCAAATA AAACGAAAGG

1601 CTCAGTCGAA AGACTGGGCC TTTCGTTTTA TCTGTTGTTT GTCGGTGAAC
                                          XbaI
1651 GCTCTCCTGA GTAGGACAAA TCCGCCGCTC TAGAGCTGCC TCGCGCGTTT

1701 CGGTGATGAC GGTGAAAACC TCTGACACAT GCAGCTCCCG GAGACGGTCA

1751 CAGCTTGTCT GTAAGCGGAT GCCGGGAGCA GACAAGCCCG TCAGGGCGCG

1801 TCAGCGGGTG TTGGCGGGTG TCGGGCGCA GCCATGACCC AGTCACGTAG

1851 CGATAGCGGA GTGTATACTG GCTTAACTAT GCGGCATCAG AGCAGATTGT

1901 ACTGAGAGTG CACCATATGC GGTGTGAAAT ACCGCACAGA TGCGTAAGGA

1951 GAAAATACCG CATCAGGCGC TCTTCCGCTT CCTCGCTCAC TGACTCGCTG

2001 CGCTCGGTCT GTCGGCTGCG GCGAGCGGTA TCAGCTCACT CAAAGGCGGT

2051 AATACGGTTA TCCACAGAAT CAGGGGATAA CGCAGGAAAG AACATGTGAG

2101 CAAAAGGCCA GCAAAAGGCC AGGAACCGTA AAAAGGCCGC GTTGCTGGCG

2151 TTTTCCATA GGCTCCGCCC CCTGACGAG CATCACAAAA ATCGACGCTC

2201 AAGTCAGAGG TGGCGAAACC CGACAGGACT ATAAAGATAC CAGGCGTTTC

2251 CCCCTGGAAG CTCCCTCGTG CGCTCTCCTG TTCCGACCCT GCCGCTTACC

2301 GGATACCTGT CCGCCTTTCT CCCTTCGGGA AGCGTGGCGC TTTCTCAATG

2351 CTCACGCTGT AGGTATCTCA GTTCGGTGTA GGTCGTTCGC TCCAAGCTGG

2401 GCTGTGTGCA CGAACCCCCC GTTCAGCCG ACCGCTGCGC CTTATCCGGT

2451 AACTATCGTC TTGAGTCCAA CCCGGTAAGA CACGACTTAT CGCCACTGGC

2501 AGCAGCCACT GGTAACAGGA TTAGCAGAGC GAGGTATGTA GGCGGTGCTA

2551 CAGAGTTCTT GAAGTGGTGG CCTAACTACG GCTACACTAG AAGGACAGTA

2601 TTTGGTATCT GCGCTCTGCT GAAGCCAGTT ACCTTCGGAA AAAGAGTTGG

2651 TAGCTCTTGA TCCGGCAAAC AAACCACCGC TGGTAGCGGT GGTTTTTTTG
```

FIG. 3c

```
2701 TTTGCAAGCA GCAGATTACG CGCAGAAAAA AAGGATCTCA AGAAGATCCT
2751 TTGATCTTTT CTACGGGGTC TGACGCTCAG TGGAACGAAA ACTCACGTTA
2801 AGGGATTTTG GTCATGAGAT TATCAAAAAG GATCTTCACC TAGATCCTTT
2851 TAAATTAAAA ATGAAGTTTT AAATCAATCT AAAGTATATA TGAGTAAACT
2901 TGGTCTGACA GTTACCAATG CTTAATCAGT GAGGCACCTA TCTCAGCGAT
2951 CTGTCTATTT CGTTCATCCA TAGCTGCCTG ACTCCCGTC GTGTAGATAA
3001 CTACGATACG GGAGGGCTTA CCATCTGGCC CCAGTGCTGC AATGATACCG
3051 CGAGACCCAC GCTCACCGGC TCCAGATTTA TCAGCAATAA ACCAGCCAGC
3101 CGGAAGGGCC GAGCGCAGAA GTGGTCCTGC AACTTTATCC GCCTCCATCC
3151 AGTCTATTAA TTGTTGCCGG GAAGCTAGAG TAAGTAGTTC GCCAGTTAAT
3201 AGTTTGCGCA ACGTTGTTGC CATTGCTACA GGCATCGTGG TGTCACGCTC
3251 GTCGTTTGGT ATGGCTTCAT TCAGCTCCGG TTCCCAACGA TCAAGGCGAG
3301 TTACATGATC CCCCATGTTG TGCAAAAAAG CGGTTAGCTC CTTCGGTCCT
3351 CCGATCGTTG TCAGAAGTAA GTTGGCCGCA GTGTTATCAC TCATGGTTAT
3401 GGCAGCACTG CATAATTCTC TTACTGTCAT GCCATCCGTA AGATGCTTTT
3451 CTGTGACTGG TGAGTACTCA ACCAAGTCAT TCTGAGAATA GTGTATGCGG
3501 CGACCGAGTT GCTCTTGCCC GGCGTCAATA CGGGATAATA CCGCGCCACA
3551 TAGCAGAACT TTAAAAGTGC TCATCATTGG AAAACGTTCT TCGGGGCGAA
3601 AACTCTCAAG GATCTTACCG CTGTTGAGAT CCAGTTCGAT GTAACCCACT
3651 CGTGCACCCA ACTGATCTTC AGCATCTTTT ACTTTCACCA GCGTTTCTGG
3701 GTGAGCAAAA ACAGGAAGGC AAAATGCCGC AAAAAAGGGA ATAAGGGCGA
3751 CACGGAAATG TTGAATACTC ATACTCTTCC TTTTTCAATA TTATTGAAGC
3801 ATTTATCAGG GTTATTGTCT CATGAGCGGA TACATATTTG AATGTATTTA
3851 GAAAAATAAA CAAATAGGGG TTCCGCGCAC ATTTCCCCGA AAAGTGCCAC
3901 CTGACGTCTA AGAAACCATT ATTATCATGA CATTAACCTA TAAAAATAGG
3951 CGTATCACGA GGCCCTTTCG TCTTCAC
```

FIG. 3d

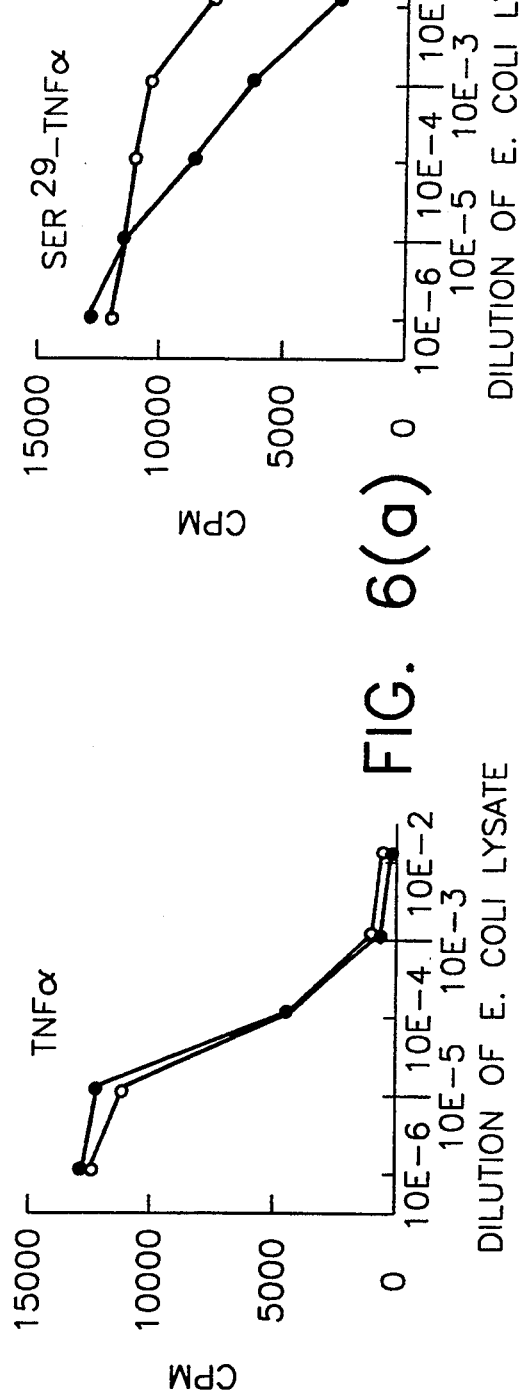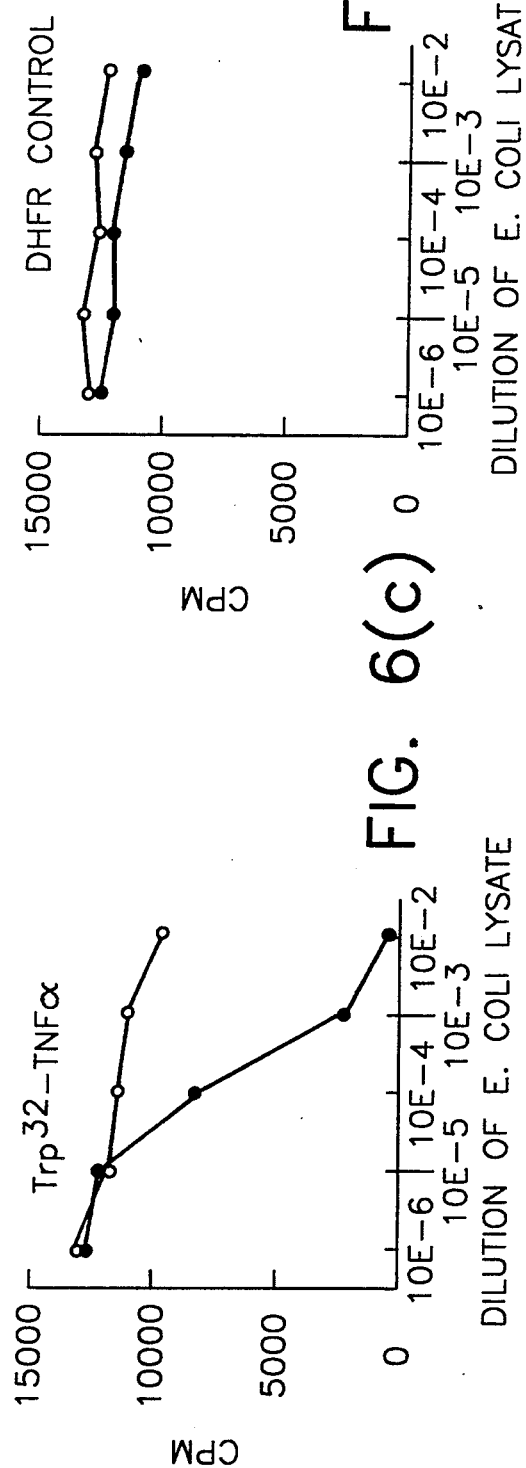

TNF-MUTEINS

BACKGROUND OF INVENTION

Tumor Necrosis Factor, or more specifically Tumor Necrosis Factor-alpha, is a cytokine, primarily produced by stimulated macrophages, that exhibits not only a striking cytotoxicity against various tumour cells [Carswell et al., Procd. Nat. Acad. Sci., U.S.A. 72, 3666–3670, (1975)]but also plays a multiple role as a mediator of inflammation and the immune response [See. Beutler and Cerami, Ann. Rev. Immunol. 7, 625–655 (1989); Bonavista and Granger (eds.) "Tumor Necrosis Factor: Structure, Mechanism of Action, Role in Disease and Therapy, Karger, Basel (1990)]. The primary structure of human Tumor Necrosis Factor-alpha (hTNF-α) has been deduced from the nucleotide sequence of a cDNA which has been cloned and expressed in *E. coli* [Pennica et al., Nature 312, 724–729 (1984); Marmenout et al., Europ. J. Biochem. 152, 515–522 (1985); Wang et al., Science 226, 149–154 (1985); Shirai et al., Nature 313, 803–806 (1985)]. A striking homology in amino acid sequence (30%) was found between hTNF-α and human Lymphotoxin, often referred to as human Tumor Necrosis Factor-beta (hTNF-β), a cytokine produced by a subset of lymphocytes [Gray et al., Nature 312, 721–724 (1984); Fiers et al., Cold Spring Harbour Symp. 51, 587–595 (1986)].

hTNF-α with modified amino acid sequences, so called TNF-α-muteins, have also been described in the art [See, e.g., Yamagishi et al., Protein Engineering 3, 713–719, (1990) or by Fiers in "Tumor Necrosis Factors: Structure, Function and Mechanism of Action", Aggarwal and Vilcek (eds.), Marcel Dekker, Inc., New York, (in press), or by Fiers et al. in Bonavista and Granger, pp. 77–81 supra. In addition TNF-α-muteins have also been the object of several patent applications, for example, International Patent Applications Publ. Nos. WO 86/02381, WO 86/04606, WO 88/06625 and European Patent Applications Publ. Nos. 155,549; 158,286; 168,214; 251,037 and 340,333, and Deutsche Offenlegungsschrift Nr. 3843534.

Muteins of Lymphotoxin have also been disclosed in the art, for example in European Patent Applications Publ. Nos. 250,000; 314,094 and 336,383.

The biological effects of TNF are mediated via specific receptors, namely a receptor with an apparent molecular weight of 55 kD on sodium dodecylsulfate polyacrylamide gel electrophoresis (SDS-PAGE) (p55-TNF-R) and a receptor with an apparent molecular weight of 75 kD on SDS-PAGE (p75-TNF-R). Both forms of TNF-receptors have been cloned previously. The cloning of p55-TNF-R was done by Loetscher et al. [Cell 61, 351–359, (1990)] and the cloning of p75-TNF-R was done by Dembic et al. [Cytokine 2, 53–58, (1990)] See also European Patent Application No. 90116707.2 (both receptors). It was found more recently that both receptors bind not only TNF-α, but also TNF-β with high affinity [Schönfeld et al., J. Biol. Chem. 266, 3863–3869 (1991)].

SUMMARY OF THE INVENTION

An object of the present invention is a mutein or a pharmaceutically acceptable salt thereof of human Tumor Necrosis Factor having an amino acid sequence which is changed by deletion, insertion and/or substitution of one or more amino acids such that the mutein shows a significant difference between its binding affinity to the human p75-Tumor-Necrosis-Factor-Receptor and the human p55-Tumor-Necrosis-Factor-Receptor.

A preferred embodiment of the present invention is a mutein as defined above on the basis of the amino acid sequence of TNF-α as disclosed by Pennica et al. supra, namely [SEQ ID No: 1]

| 1 | | | | | | | | | 10 | | | | | |
|---|---|---|---|---|---|---|---|---|---|---|---|---|---|---|
| VAL | ARG | SER | SER | SER | ARG | THR | PRO | SER | ASP | LYS | PRO | VAL | ALA | HIS |
| | | | | 20 | | | | | | | | | | 30 |
| VAL | VAL | ALA | ASN | PRO | GLN | ALA | GLU | GLY | GLN | LEU | GLN | TRP | LEU | ASN |
| | | | | | | | | | 40 | | | | | |
| ARG | ARG | ALA | ASN | ALA | LEU | LEU | ALA | ASN | GLY | VAL | GLU | LEU | ARG | ASP |
| | | | | 50 | | | | | | | | | | 60 |
| ASN | GLN | LEU | VAL | VAL | PRO | SER | GLU | GLY | LEU | TYR | LEU | ILE | TYR | SER |
| | | | | | | | | | 70 | | | | | |
| GLN | VAL | LEU | PHE | LYS | GLY | GLN | GLY | CYS | PRO | SER | THR | HIS | VAL | LEU |
| | | | | 80 | | | | | | | | | | 90 |
| LEU | THR | HIS | THR | ILE | SER | ARG | ILE | ALA | VAL | SER | TYR | GLN | THR | LYS |
| | | | | | | | | | 100 | | | | | |
| VAL | ASN | LEU | LEU | SER | ALA | ILE | LYS | SER | PRO | CYS | GLN | ARG | GLU | THR |
| | | | | 110 | | | | | | | | | | 120 |
| PRO | GLU | GLY | ALA | GLU | ALA | LYS | PRO | TRP | TYR | GLU | PRO | ILE | TYR | LEU |
| | | | | | | | | | 130 | | | | | |
| GLY | GLY | VAL | PHE | GLN | LEU | GLU | LYS | GLY | ASP | ARG | LEU | SER | ALA | GLU |
| | | | | 140 | | | | | | | | | | 150 |
| ILE | ASN | ARG | PRO | ASP | TYR | LEU | ASP | PHE | ALA | GLU | SER | GLY | GLN | VAL |
| | | | | | 157 | | | | | | | | | |
| TYR | PHE | GLY | ILE | ILE | ALA | LEU | | | | | | | | | or as disclosed by Marmenout et al. supra or Wang et al. supra or Shirai et al. supra. More specifically muteins of deduced amino acid sequence as are coded for by the nucleotide sequence of the insert of the plasmid pDS56/RBSII,Sph1-TNFα [SEQ ID No: 2] (See also FIG. 3a and 3B) coding for mature TNF-α.

Another preferred embodiment of the present invention is a mutein as defined above wherein the TNF-α amino acid sequence is changed by substitution of one or more amino acids, preferably one or two by other amino acids, and preferably by naturally occuring amino acids.

Another preferred embodiment is a human Tumor Necrosis Factor mutein wherein SEQ ID NO: 1 is changed by deletion, insertion, substitution or combinations thereof, of between one and 10 amino acids.

A more preferred embodiment of the present invention are muteins as defined above wherein the TNF-α amino acid sequence is substituted at position 29 and/or 32 or position 31 and 32 or position 31 or position 29 and 31 whereby substitutions at position 29 and/or 32 or position 31 and 32 or position 31 are preferred (referring to [SEQ ID No:1]) by other amino acids, preferably naturally occuring amino acids. Any amino acid, preferably any naturally occuring one, can be used at one or more of these positions which leads to a TNF-mutein showing a significant difference between its binding affinity to the human p75-TNF-R and the human p55o TNF-R. For substitutions at position 29 serine [SEQ ID No:4], glycine [SEQ ID No:5] or tyrosine [SEQ ID No:6] are preferred, serine is especially preferred, for example in case of a single position mutein at position 29 ($Ser^{29}$-TNFα) [SEQ ID No:4]. For substitutions at position 31 glutamic acid, for example $Glu^{31}$-TNFα[SEQ ID No:7], or asparagine [SEQ ID No: 8] are preferred. For substitutions at position 32 tyrosine, for example $Tyr^{32}$-TNFα[SEQ ID No:10] or tryptophan, for example $Trp^{32}$-TNFα [SEQ ID No:9] are preferred, $Trp^{32}$ is specifically preferred. Especially preferred substitutions in case of a double position mutein at positions 29 and 32 are $Ser^{29}$-$Trp^{32}$-TNFα [SEQ ID No: 12] and at position 31 and 32 are $Asn^{31}$-$Thr^{32}$-TNFα. [SEQ ID No: 11]. It is understood that the muteins of the present invention can also be prepared by methods known in the art of chemical peptide and protein synthesis, for example by partial or total liquid or solid phase synthesis as described by Gross and Meyenhofer in "The Peptides" Vols. 1-9, Academic Press, Inc., Harcourt Brace Jovanovich, Publs., San Diego (1979-1987) or by Fields and Nobel, Int. J. Pept. Prot. Res. 35, 161-214 (1990).

Another preferred embodiment of the present invention is a mutein of TNF-α comprising the amino acid sequence set forth in SEQ ID No: 1 wherein at lease one of the positions 29, 31 or 32 is substituted with any naturally occurring amino acid different from the corresponding amino acid in SEQ ID No: 1.

Analogs obtained by deletion, substitution or addition or combinations thereof of one or several amino acids from or to the muteins as defined in the previous paragraph, whereby position 29 and/or 32 or position 31 or position 31 and 32 in the mutein are not changed and which analogs still show a significant difference between its binding affinity to the human p75-TNF-R and the human p55-TNF-R are also an object of the present invention. With respect to such substitution analogs, amino acid substitutions in proteins which do not generally alter the activity are known in the state of the art and are described, for example, by H. Neurath and R. L. Hill in "The Proteins" (Academic Press, New York, 1979, see especially FIG. 6, page 14). The most commonly occurring exchanges are: Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly as well as these in reverse (the three letter abbreviations are used for amino acids and are standard and known in the art).

Analogs made by substitution, addition, deletion or combinations thereof can be produced by methods known in the art and described for example in Sambrook et al. [Molecular Cloning, A Laboratory Manual, 2nd ed., Cold Spring Harbour Laboratory, Cold Spring Harbour Laboratory Press, USA (1989)] or as described herein. Whether such an analog still shows the significant difference between its binding affinity to the p75-TNF-R and the p55-TNF-R can be determined as described below and more specifically in Examples II1) and 2) or Example VIII. Furthermore, salts of such muteins and analogs are also an object of the present invention. Such salts can be produced by methods known in the art.

It is furthermore an object of the present invention to provide a mutein as described above for the treatment of illnesses, for example cancer.

It is well known in the art that on the basis of its biological activities TNF-α can be a valuable compound for the treatment of various disorders. For example TNF-α, alone or in combination with interferon, can be an effective antitumor agent [Brouckaert et al., Int. J. Cancer 38, 763-769 (1986)]. However, its systemic toxicity is a major limitation to its wider therapeutic use [Taguchi T. and Sohmura Y., Biotherapy 3, 177-186 (1991)].

The discovery of two TNF-receptors with (putatively) distinct functional roles should allow one to separate in a given disease state the benefical and unwanted biological responses to TNF. There is circumstantial evidence supporting the feasibility of this approach. It has been shown for example [Brouckaert et al., Agents and Actions 26, 196-197 (1989); Everaerdt, B. et al., Biochem. Biophys. Res. Comm. 163, 378-385 (1989)] that in mice, murine TNF-α (mTNF-α)is up to 50-fold more toxic than human TNF-α (hTNF-α), although when tested in cell culture (murine and human), both are equally active on sensitive cell lines.

It is believed that the strategy of separating beneficial and unwanted TNFα activities by using compounds specifically binding to one or the other TNF-receptor, such as the TNF-muteins of the present invention, can be used in general in other disease states where TNF plays a role.

DNA-sequences comprising a DNA-sequence coding for TNF-muteins as hereinbefore described are also an object of the present invention. Such DNA-sequences can be constructed starting from genomic-or cDNA-sequences coding for hTNF as disclosed in the art using known methods of in vitro mutagenesis [see e.g. Sambrook et al., 1989]. Such mutagenesis can be carried out at random in order to obtain a large number of mutants which can then be tested for their desired properties in appropriate assay systems or, in order to mutate defined positions in a given DNA-sequence, by so called site directed mutagenesis [see, e.g., Sambrook et al., 1989, 15.51-15.113] or by mutagenesis using the polymerase chain reaction [see, e.g., White et al., Trends in Genetics 5, 185-189 (1989)].

A preferred embodiment of the invention is a purified and isolated DNA sequence comprising positions 115 to 591 of SEQ ID NO:2 wherein the DNA sequence is changed by deletion, insertion, substitution or combinations thereof, such that the DNA sequence codes for a human Tumor Necrosis Factor mutein containing at least one amino acid different from SEQ ID No: 1 and the mutein shows a significant difference between its binding affinity to the human p75-(Tumor Necrosis Factor)-Receptor and to human p55-(Tumor Necrosis Factor)-Receptor.

Another preferred embodiment is a purified and isolated DNA sequence comprising positions 115 to 591 of SEQ ID No: 13 wherein at least one of the codons at positions 202 to 204, 208 to 210, or 211 to 213 codes for an amino acid different from the amino acid coded for by the corresponding condon in SEQ ID No: 2.

One chemical mutagen which is often used for random mutagenesis is sodium bisulfite which converts cytosin residues into uracil residue and hence leads to a transition of "C" to "T" (standard abbreviations for nucleotides) [for the method see e.g. Shortle and Nathans, Procd. Nat. Acad. Sci. U.S.A. 75, 2170–2174

(1978) or Pine and Huang, Meth. Enzym. 154, 415–430 (1987)]. This mutagen acts solely on single stranded DNA whereas the expression of the mutated target DNA sequence is achieved with a double stranded plasmid vector. One possibility to avoid the necessity of recloning in mutagenesis and expression vectors is the use of so called "phasmids". These are vectors which, in addition to a plasmid origin of replication, carry also an origin of replication derived from a filamentous phage. Examples of such phasmids are the pMa-and pMcphasmids as described by Stanssen et al. [Nucleic Acids Res. 17, 4441–4454, (1989)]. Using this expression system one can construct so called "gap-duplex"-structures [see also Kramer et al., Nucl. Acids. Res. 12, 9441–9456 (1984)] where only the TNF-coding sequence is in a single stranded configuration and therefore accessible for the specific chemical mutagen. "Gap-duplexes" to be used in at random mutagenesis can be constructed as described for site-specific mutagenesis by Stanssen et al. supra with the exception that the (−)strand contains the same active antibiotic resistance gene as the (+)strand. By making use of different restriction sites in the DNA-sequence encoding hTNFα [SEQ ID No:2], variation of the width of the gap is possible. Examples of such restriction sites are the ClaI-SalI sites (470 nucleotides), BstXI-BstXI sites (237 nucleotides) or StyI-StyI sites (68 nucleotides). Such gap-duplex-constructs can then be treated with increasing concentrations (up to 4M) of bisulfite, followed by several dialysis steps, as described by Shortle and Nathans supra. A suitable procaryotic host cell can then be transformed by such phasmid constructs according to methods known in the art and described for example by Sambrook et al. supra. A suitable procaryotic host cell means in this context a host cell deficient in a specific repair function so that an uracil residue is maintained in the DNA during replication and which host cell is capable of expressing the corresponding mutated TNF. Such specific host strains are known in the art, for example for *E. coli* strains, e.g. *E. coli* BW 313 [Kunkel, T.A., Procd. Natl. Acad. Sci. USA 82, 488–492 (1985)]. The resulting clones can then be screened for those expressing a desired TNF-mutein by appropriate assay systems. For example each colony can be inoculated in a microtiterplate in a suitable medium containing the relevant antibiotic. The cells may be lysed by addition of lysozyme, followed by sequential freeze-thaw cycles. After precipitation of nucleic acids and centrifugation, the supernatant of each colony can directly be used in appropriate assays as described, for example, in Example IIa and IIb or Example VIII measuring binding to the p75-TNF-R and the p55-TNF-R on the surface of living cells or in purified form.

If desired, the specific sites of mutation can be determined, for example by restriction fragment analysis [see, e.g., Sambrook et al. Supra]. By determination of the DNA-sequence of such fragments the exact position of the mutation can be determined and if such mutation leads to an amino acid replacement the new amino acid can be derived from the determined DNA-sequence. DNA-sequencing can be performed according to methods known in the art, for example by using T7 polymerase on supercoiled DNA with a commercially available sequencing kit (Pharmacia, Uppsala, Sweden).

As already mentioned above, another possibility of mutating a given DNA-sequence is by "site directed mutagenesis". A widely used strategy for such kind of mutagenesis as originally outlined by Hutchinson and Edgell [J. Virol. 8, 181 (1971)] involves the annealing of a synthetic oligonucleotide carrying the desired nucleotide substitution to a target region of a single stranded DNA-sequence wherein the mutation should be introduced [for review see Smith, Annual. Rev. Genet. 19,423 (1985) and for improved methods see references 2–6 in Stanssen et al. supra.

One such preferred method is the one of Stanssen et al. supra (1989) using "gapped duplex DNA" as originally described by Kramer et al. supra (1984) [see also Kramer and Fritz, Methods in Enzymology, (1987), Academic Press, Inc., USA], but using antibiotic resistance genes instead of M13 functional genes for selection of the mutation containing strand as well as the phasmid-technology described by Stanssen et al. supra (1989). An advantage of this method lies also in the capability of performing successive cycles of mutagenesis without the need to transfer the gene to a new mutagenesis vector. The second round mutagenesis differs only in the selection using another antibiotic marker (Stanssen et al., supra). As a control, site-specific back mutagenesis of the mutant to the wild-type TNF can be used. In addition, the use of an oligonucleotide, creating or destroying a restriction site in the TNF gene, allows one to control the mutant not only by hybridization to the oligonucleotide used for site directed mutagenesis but also by the presence or absence of the restriction site. In order to create a set of TNF-muteins wherein at a defined position of their amino acid sequence the wild-type amino acid, is replaced by any naturally occurring amino acid a set of oligonucleotides is used with all possible codons at the defined position.

As already mentioned above, another possibility of mutating a given DNA-sequence is the mutagenesis by using the polymerase chain reaction (PCR). The principle of this method is outlined by White et al. supra (1989), whereas improved methods are described in Innis et al. [PCR Protocols: A Guide to Methods and Applications, Academic Press, Inc. (1990)].

PCR is an in vitro method for producing large amounts of a specific DNA fragment of defined length and sequence from small amounts of a template DNA. PCR is based on the enzymatic amplification of the DNA fragment which is flanked by two oligonucleotide primers that hybridize to opposite strands of the target sequence. The primers are oriented with their 3' ends pointing towards each other. Repeated cycles of heat denaturation of the template, annealing of the primers to their complementary sequences and extension of the annealed primers with a DNA polymerase result in the amplification of the segment defined by the 5' ends of the PCR primers. Since the extension product of each primer can serve as a template for the other, each cycle essentially doubles the amount of the DNA fragment produced in the previous cycle. Since the primers are physically incorporated into the amplified product and mismatches between the 5' end of the primer and the template do not significantly affect the efficiency of the amplification, it is possible to alter the amplified sequence thereby introducing the desired mutation into the amplified DNA. By utilizing the thermostable Taq DNA polymerase isolated from the thermophilic bacteria Thermus aquaticus, it has been possible to avoid denaturation of the polymerase which necessitated the addition of enzyme after each heat denaturation step. This development has led to the automation of PCR by a variety of simple temperature-cycling devices. In addition, the specificity of the amplification reaction is increased by allowing the use of higher temperatures for primer annealing and extension. The increased specificity improves the overall yield of amplified products by minimizing the competition from non-target fragments for enzyme and primers.

Design and synthesis of oligonucleotides can be effected as known in the art and described, for example, in Sambrook et al. supra (1989) or in one of the references cited above with respect to site-directed mutagenesis.

As soon as a DNA-sequence coding for a TNF-mutein of the present invention has been created, expression can be effected by the phasmid technology as described above or by use of any suitable pro- or eukaryotic expression system well known in the art [see, e.g., Sambrook et al., supra,].

Expression is effected preferably in prokaryotic cells, for example, in E. coli, Bacillus subtills and so on, whereby E. coli, specifically E. coli K12 strains for example M15 [described as DZ 291 by Villarejo et al. in J. Bacteriol. 120 J, 466–474 (1974)], HB 101 [ATCC No. 33694], WK6 (Stanssens et al. supra) or E. coli SG13009 [Gottesman et al., J. Bacteriol. 148, 265–273 (1981)] are preferred. Expression of the muteins of the present invention can also be effected in lower or higher eukaryotic cells, like for example yeast cells (like Saccharomyces, Pichia etc.), filamentous fungi (like Aspergillus etc.) or cell lines (like chinese hamster ovary cell lines etc.), whereby expression in yeast cells is preferred [see Sreekrishna et al., Biochem. 28, 4117–4125, ( 1989 ); Hitzeman et al., Nature 293, 717–722 (1981); European Patent Application Publication No. 263 311]. Expression of the TNF-muteins of the present invention may occur in such systems either intracellularly, or, after suitable adaption of the gene, extracellularly (see Leemans et al., Gene 85, 99–108, 1989).

Suitable vectors used for expression in E. coli are mentioned e.g. by Sambrook et al. [supra] or by Fiers et al. in "Procd. 8th Int. Biotechnology Symposium" [Sot. Franc. de Microbiol., Paris, (Durand et al., eds.), pp. 680–697 (1988)] or and more specifically vectors of the pDS family [Bujard et al., Methods in Enzymology, eds. Wu and Grossmann, Academic Press, Inc. Vol. 155, 416–433 (1987); St0ber et al., Immunological Methods, eds. Lefkovits and Pernis, Academic Press, Inc., Vol. IV, 121–152 (1990)] like, for example, pDS56/RBSII,Sph1-TNFα Ser29 or pDS56/RBSII,Sph1-TNFαTrp32 (see Example I) or pDS56/RBSII,Sph1-TNFα Glu31 or pDS56/RBSII,Sph1-TNFα Asn31Thr32 (see Example VII). The transformed E. coli strains M15 (pREP4;pDS56/RBSII,Sph1-TNFαGlu31) and M15 (PREP4;pDS56/RBSII,Sph1-TNFαAsn31Thr32) have been deposited under the Budapest Treaty for patent purposes at the Deutsche Sammlung von Mikroorganismen und Zellkulturen GmbH (DSM) in Braunschweig, BRD at September 8th, 1991 under accession numbers DSM 6714 and DSM 6715 respectively. These specific pDS56/RBSII-plasmids with their specific regulatable promoter/operator elements and ribosomal binding sites can achieve a high level of expression. Therefore, the plasmids can be maintained in E. coli cells only when the activity of the promoter/operator element is repressed by the binding of a lac repressor to the operator. The activity of the promoter can be restored when the culture has reached the desired cell density by addition of isopropyl-β-D-thio-galacto-pyranoside (IPTG), which inactivates the repressor and clears the promoter. Since most of the E. coli strains do not provide enough repressor molecules to completely repress the function of the promoter sequences present in these high copy number plasmids, such E. coli strains, E. coli M15 or SG13009, have to be first transformed with a plasmid, such as pREP 4, which codes for the lac repressor, before being transformed with the specific pDS56/RBSII-plasmids of the invention which thereafter can be stably maintained in the E. coli cells. In addition to coding for the lac repressor, pREP4 also contains a region of the plasmid pACYC184 [Chang and Cohen, J. Bacteriol. 134, 1141–1156 (1978)], which contains all information required for replication and stable transmission to daughter cells. The DNA sequence of pREP4 is set out in FIG. 2b and SEQ ID No: 14 [see also "System for high level production in E. coli and rapid purification of recombinant proteins: application to epitope mapping, preparation of antibodies and structure function analysis" by Stüber et al. in Immunological Methods, Vol. IV, pp 121–152, Lefkovits and Pernis (eds.), Academic Press, New York (1990)].

A preferred embodiment of the present invention is an expression vector suitable for producing a human Tumor Necrosis Factor mutein comprising the amino acid sequence set forth in SEQ ID No: 1 wherein SEQ ID No: 1 is changed by deletion, insertion, substitution or combinations thereof, of at least one amino acid so that the mutein shows a significant difference between its binding affinity to the human p75-(Tumor Necrosis Factor)-Receptor and to human p55-Tumor Necrosis Factor)Receptor when the vector is stably transformed or transfected in a prokaryotic or lower eukaryotic host cell.

Another preferred embodiment of the present invention is a vector comprising SEQ ID No: 2 wherein the DNA sequence comprising positions 115 to 591 is changed by deletion, insertion, substitution or combinations thereof.

Transformation of the host cells by vectors as described above may be carried out by any conventional procedure [see, e.g., Sambrook et al. supra]. Where the host cell is a prokaryote, such as E. coli for example, competent cells which are capable of DNA uptake are prepared from cells harvested after exponential growth phase and subsequently treated according to the known $CaCl_2$-method. Transformation can also be performed after forming a protoplast of the host cell or by other methods known in the art and described, for example in Sambrook et al. Therefore a vector, especially for expression in a prokaryotic or lower eukaryotic host cell, comprising a DNA-sequence coding for a TNF-mutein as described above, and a host cell, especially a prokaryotic host cell, for example, E. coli, or a lower eukaryotic host cell, transformed by such a vector are also an object of the present invention.

Usually, the host organisms which contain a desired expression vector are grown under conditions which are optimal for their growth. In case of a procaryotic host at the end of the exponential growth, when the increase in cell number per unit time decreases, the expression of the desired TNF-mutein is induced, that is the DNA coding for the desired TNF-mutein is transcribed and the transcribed mRNA is translated. The induction can be carried out by adding an inducer or a derepressor to the growth medium or by altering a physical parameter, for example a change in temperature. In the expression vectors used in the preferred embodiments of the present invention, the expression is controlled by the lac repressor. By adding IPTG, the expression control sequence is derepressed and the synthesis of the desired TNF-mutein is thereby induced.

A preferred embodiment of the present invention is a prokaryotic or lower eukaryotic host cell stably transformed or transfected with a vector suitable for producing a human Tumor Necrosis Factor mutein comprising the amino acid sequence set forth in SEQ ID No: 1 wherein SEQ ID No: 1 is changed by deletion, insertion, substitution or combinations thereof, of at least one amino acid so that the mutein shows a significant difference between its binding affinity to the human p75-(Tumor Necrosis Factor)-Receptor and to human p55-(Tumor Necrosis Factor)-Receptor.

Another preferred embodiment of the present invention is a host cell which is stably transformed or transfected with an expression vector comprising positions 115 to 591 of SEQ ID No:2 and in which the DNA sequence is changed by deletion, insertion, substitution or combinations thereof, such that the DNA sequence codes for a human Tumor Necrosis Factor mutein containing at least one amino acid different from SEQ ID No:1.

TNF-muteins of the present invention produced by transformed host cells as stated above can be recovered from the culture medium or after opening the cells with or without extraction by any appropriate method known in protein and peptide chemistry such as, for example, precipitation with ammonium sulfate, dialysis, ultrafiltration, gelfiltration or ion-exchange chromatography, gel electrophoresis, isoelectric focusing, affinity chromatography, like immunoaffinity chromatography, HPLC or the like. Specifically preferred methods are precipitation with ammonium sulfate and/or polyethylenimine, dialysis, affinity chromatography, for example on phenyl-agarose, specifically phenyl-sepharose, or ion-exchange chromatography, specifically on a MONO-Q-and/or MONO-S-matrix (Pharmacia, Uppsala, Sweden) or more specifically preferred are those as described by Tavernier et al. [J. Mol. Biol. 211,493-501 (1990)] and those disclosed in Example I or Example III.

It is therefore also an object of the present invention to provide a process for the preparation of a compound as specified above which process comprises cultivating a transformed host cell as described above in a suitable medium and isolating a mutein from the culture supernatant or the host cell itself, and if desired converting said mutein into a 2.5 pharmaceutically acceptable salt. The compounds whenever prepared according to such a process are also an object of the present invention.

The muteins of the present invention are characterized by showing a significant difference between its binding affinity to the human p75-TNF-R and the human p55-TNF-R. Such property can be determined by any assay known in the art measuring binding affinities. For example, the binding of TNF itself and of the muteins of the present invention can be measured using cells in cell culture which express the two types of TNF-receptors to a different degree, for example Hep-2 cells which exclusivly s5 express the human p55-TNF-R and U937 or HL60 cells which express both the human p55-TNF-R and the human p75-TNF-R [see Brockhaus et al., Procd. Nat. Acad. Sci. U.S.A. 87, 3127-3131, (1990); Hohmann et al., J. Biol. Chem. 264, 14927-14934, (1989); Loetscher et al. (1990); Dembic et al. (1990)]. Of course binding affinities can also be determined directly by using purified native or recombinant p55-TNF-R and p75-TNF-R as specifically described in Example 112, or by using the corresponding soluble analogs of such receptors.

The term "significant difference between its binding affinity to the human p75-Tumor-Necrosis-Factor-Receptor (p75-TNF-R) and to the human p55-Tumor-Necrosis-Factor-Receptor" (p55-TNF-R) refers, the context of the present invention, to a difference in binding affinities to the two types of TNF-receptors which is with respect to the assay system used, significant enough to say that a mutein of the present invention binds preferentially to one of the two TNF-receptors as compared to wild type TNF. The binding affinity for the p55-TNF-R expressed as a $K_D$-value is measured using Hep-2 cells which only carry that receptor. The binding affinity for the p75-TNF-R is measured using the U937 cells which predominantly, but not exclusively carry the p75 receptor. In terms of the assay system described in Example II (b)(iii)(Table E), the muteins of the present invention differ in their binding affinities to p55-TNF-R and p75-TNF-R by a factor in the range from about 10 to more than 200. A preferential upper limit of this range is 1000 and a most preferential upper limit of this range is 10000. More specifically this term means in the context of the assay-system of Example II (b)(iii) that a $K_D$-value of a specific TNF-mutein of the present invention is at least a factor of 10 or more, especially preferred at least a factor of $10^2$ larger than for TNF-$\alpha$ itself determined by using U937 cells whereby its $K_D$-value determined by using Hep-2 cells for the same TNF-mutein is not larger than a factor of 2 as for TNF-$\alpha$ itself [for specific data see Table E]. It is however understood that these specific $K_D$-values are given for illustration and should not be considered as limiting in any manner. Since the purified receptors bind TNFα in the filter binding assays of the present invention with high affinity (see Schönfeld et al., J. Biol. Chem. 266, 3863-3869), namely for the p75-TNF-R with a $K_D$ of $1.0 \times 10$ μM and for the p55-TNF-R with a KD of $16 \times 10^{-11}$M the preferential binding of the muteins of the present invention to one of the two TNF-receptors can be also illustrated by a so called selectivity factor "S" which is defined in the following manner:

$$S = \frac{IC50 \text{ p75-TNF-R}}{IC50 \text{ p55-TNF-R}}$$

"IC50 p75-TNF-R" or "1C50 p55-TNF-R" stands for the concentration of a mutein of the present invention which concentration leads to a 50% inhibition of the binding of TNFα to the p75-TNF-R or p55-TNF-R in a competition assay (such values can be calculated from the data shown in FIG. 1 and FIG. 7; see Table F). Accordingly the muteins of the present invention can show an S-value in the range of 10 to at least 500, preferentially 1000 (see Table G). In addition based on the IC50-values the value of decrease of the affinity of the mutein for both receptors can be calculated (see Table F).

The muteins of the present invention can be characterized by their anti-tumour activity by methods known in the art and described for example in Example IV.

The muteins of the present invention may show considerably reduced cytotoxic activity in standard TNF-assays which are based on murine cell lines, such as L929 (see Table E) or L-M cell lines.

TNF-muteins of the present invention can be used for the treatment of illnesses, for example cancer.

A further object of the present invention is a pharmaceutical composition and a process for its preparation which composition contains one or more compounds of the invention, if desired in combination with additional pharmaceutically active substances with our without nonontoxic, inert, therapeutically compatible carrier materials. For this purpose, one or more compounds of the invention, where desired or required in combination with other pharmaceutically active substances, can be processed in a known manner with the usually used solid or liquid carrier materials. The dosage of such preparations can be effected having regard to the usual criteria in analogy to already used preparations of similar activity and structure.

A preferred embodiment of the present invention is a pharmaceutical composition comprising an effective amount of a human Tumor Necrosis Factor mutein comprising SEQ ID No: 1 in which SEQ ID No: 1 is changed by deletion, insertion, substitution or combinations thereof, of at least one amino acid so that the mutein shows a significant difference between its binding affinity to the human p75-(Tumor Necrosis Factor)-Receptor and to human p55-(Tumor Necrosis Factor)-Receptor or a pharmaceutically acceptable salt thereof and an inert carrier.

BRIEF DESCRIPTION OF THE DRAWINGS

FIGS. 2b, 2c, and 2d are the nucleotide sequence of plasmid pREP4.

FIGS. 3b, 3c, and 3d are the nucleotide sequence of plasmid pDS56/RBSII,Sph1-TNFα.

DETAILED DESCRIPTION OF THE INVENTION

After the invention has been described in general hereinbefore, the following Examples are intended to illustrate details of the invention, without thereby limiting it in any manner.

Example I

Figure 3A:
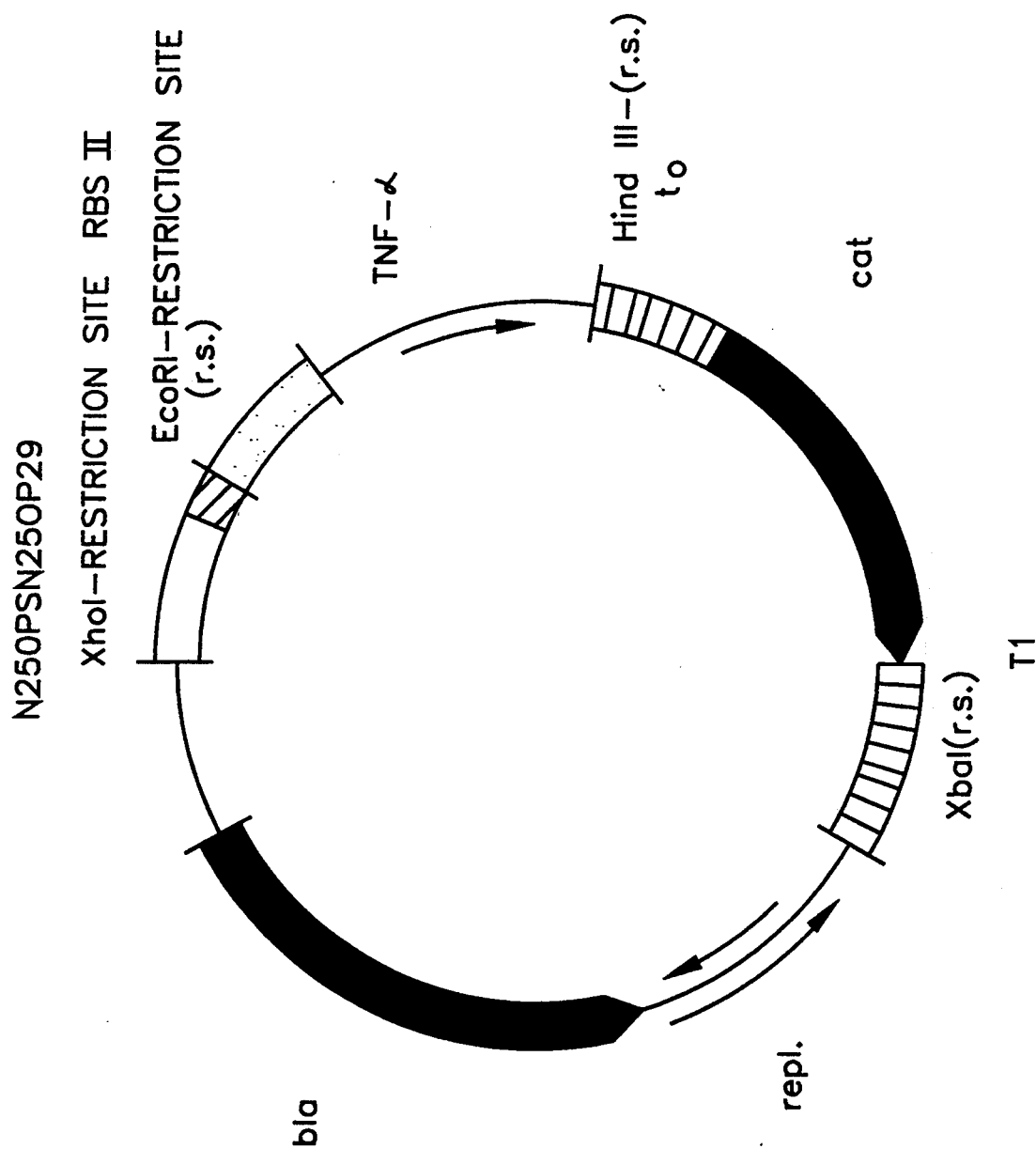
FIG. 3a is a schematic depiction of plasmid pDS56/RBSII,Sph1-TNFα.

A. Preparation of Ser$^{29}$-TNFα and Trp$^{32}$-TNFα
(1) Construction of a mutagenesis vector From the human TNF expression plasmid pDS56/RBSII,Sph1-TNFα (see FIG. 3a: The expression plasmid contain the regulatable promoter/operator element N25OPSN25OP29 (▢▨), the synthetic ribosomal binding site RBSII (▨), genes (▬▶) ribosomal binding S for β- actamase (bla), chloramphenicol acetyltransferase (cat), and transcriptional terminators (▨) to of phage lambda (to) and T1 of rrnB operon of E. coli (T1), and the replication region of plasmid pBR322 (repl.). The coding region under control of N25OPSN25OP29 and RBSII is indicated by an arrow; for complete nucleotide sequence of the plasmid see [SEQ ID No: 2] FIG. 3b/1-3b/3 given by the one letter standard abreviations for nucleotides), an EcoR1-HindIII fragment was isolated, containing the ribosome binding site RBSII, the mature TNRα coding sequence and a 130 bp 3' non-translated sequence. This fragment was cloned into the EcoR1HindIII opened pMac phasmids (Stanssens et al., supra), resulting in the constructions pMa/RBSII,Sph1-TNFα and pMc/RBSII,Sph1-TNFα.

(2) Isolation of single-stranded (ss)DNA

The pMa/RBSII,Sph1-TNFoc phasmid was transformed to E. coli WK6 (Stanssens et al., supra). One colony was picked up and cultured in 5 ml LB medium (Sambrook et al., supra 1989) with carbenicillin (50 μg/ml) at 37° C., overnight. 1 ml of this confluent culture was used to inoculate 200 ml LB containing carbenicillin. When the absorbance (650 nm) reached a value of 0.1, the culture was infected with M13K07 helper phage (Stanssens et al., (1989) at a m.o.i. of about 20 and further incubated overnight at 37° C.. Then, the cells were spun down (10 min, 10.000 rpm) and the supernatant was transferred into another tube. 50 ml PEG-solution (20% polyethylene glycol 6000; 2.5 M NaCI) was added and the mixture was kept on ice for one hour to precipitate the phageso After centrifugation (10 min; 8000 rpm), the supernatant was removed and the tube was dried on paper towels for 10 min. The phage pellet was resuspended in 6 ml TE buffer (10 mM Tris-HCl, 0.1 mM EDTA, pH8). A first extraction was performed with 6 ml TE-saturated phenol, followed by vortexing for 3 min. After centrifugation (3 min) in an Eppendorf centrifuge, the aqueous phase was transferred to a fresh tube and a second extraction was carried out with chloroform:isoamylalcohol (24:1) in the same way as described. The single stranded DNA could be precipitated by adding 1/10 volume of 5M NaClO$_4$ and 1 volume of isopropanol (−20° C., 2 hours). This ssDNA was pelleted by centrifugation for 20 min in an Eppendorf centrifuge. The pellet was dried and dissolved in 500 μl TE buffer as a control, 5 μl of this mixture was run on an agarose gel, containing 1 μg/ml ethidium bromide. Usually, the ratio of pMa/R-BSII,Sph1-TNFαssDNA (=(+)strand) over helper phage ssDNA was between 2:1 and 20:1. The amount of total ssDNA was estimated to be at least 200 ng/μl.

(3) Construction of a gap-duplex

From the phasmid pMc, the EcoR1-HindIII large fragment was isolated and used for hybridization to the pMa/RBSII, Sph1-TNFα(+)strand. In a typical experiment, 15 μl ssDNA (±3 μg), 15 μl of the double stranded, linear fragment (±1.5 μg), 10 ml hybridization buffer (1.5 M KCI; 100 mM Tris-HCI, pH 7.5) and 40 μl H$_2$O were mixed and incubated at 100° C. for 4 min, 65° C. for 8 min and room temperature for 15 min. An aliquot (10 ml) was electrophoresed on an agarose gel containing ethidium bromide, to check the formation of gap duplex DNA and, if so, to estimate its quantity (this usually amounted to 50 ng/10 ml hybridization mixture).

(4) Annealing of the mutant oligonucleotide and fill-in of the gap duplex

Oligonucleotides were synthesized containing the mutated codon and destroying or creating a restriction site in the TNF gene. The oligonucleotides 5'CCGGCGGTTGGACCACTGGAGC3'[SEQ ID No:15] and 5'CATTGGCCCAGCGGTTCAG3' [SEQ ID No: 16] (mutated bases underlined) were used to create the Ser$^{29}$ and Trp$^{32}$ mutations, respectively. After enzymatic phosphorylation, about 8 pmol was added to 40 ng of gapduplex. H$_2$O was added to a final volume of 10 ml. This mixture was heated to 65° C. for 5 min and allowed to cool to room temperature. Subsequently, 18 ml H$_2$O, 4 μl fill-in buffer 10 (625 mM KCI, 275 mMTrisHCI, 150 mM MgCl$_2$, 20 mM DTT pH 7.5), 2 μl ATP 1 mM, 4 μl of the four dNTP's 1 mM, 1 μl ligase and 1 ml Klenow polymerase were added and the mixture was incubated at room temperature for 45 min.

(5) Transformation to E. coli WK6 mutS and E. coli WK6

We used 10 ILl of the filled-in gap duplex DNA to transform (Sambrook et al., 1989) E. coli WK6 mutS (Stanssens et al., supra). From this mixture (1.2 ml), 100 ml was plated out on agar plates containing 25 μg/ml chloramphenicol to check transformation efficiency. The remainder was used to inoculate 20 ml LB+chloramphenicol and further grown overnight at 25° C. . A small-scale plasmid DNA preparation [Birnboim, H. C. and Doly, J., Nucleic Acids Res., 7, 1513, (1979)] of this culture (not yet grown to confluency) resulted in a mixed phasmid population that could be transformed to E. coli WK6. Again, 100 μl transformation mixture was plated out on agar plates containing chloramphenicol.

(6) Screening by colony hybridization

About 100 colonies, resulting from the transformation to E. coli WK6, were streaked on a nylon filter (PALL, Glen Cove, New York) and incubated overnight at 37° C. . The filter was transferred (face up) to Whatmann 3MM papers which were soaked in 0.5 M NaOH (3 min). Neutralization was done by transfer to Whatmann 3MM sheets soaked in 1M Tris-HCI pH 7.4 (twice for 1 min) and 2XSSC (20xSSC=3M NaCl; 0.3M Na citrate, pH7) (5 min). After drying, the filter was baked at 80° C. between sheets of 3MM paper. Subsequently, the filter was prewetted in 6xSSC (5 min) and prehybridized at 67° C. for 5 min in 10x Denhardt solution (2% (w/v) Ficoll (400,000 MV), 2% (w/v) Polyvinylpyrrolidone (44,000 MW), 2% (w/v) Bovine Serum Albumin), 6xSSC buffer and 0.2% SDS. After rinsing in 6xSSC buffer, the filter was placed in a Petri dish containing 4 ml 6xSSC and 60 pmol of the $^{32}$P-labeled mutant oligonucleotide for 1 hour at room temperature, and rinsed in 100 ml 6xSSC. The filter was covered with Saran ® wrap or suitable plastic film and autoradiographed on preflashed films (Fuji) at −70° C. for I hour. Subsequently, the filter was again washed in 6xSSC buffer at increasing temperatures (varying between 51° C. and 75° C. , according to the length of the probe and its amount of G and C residues), followed each time by an autoradiography, as described above. For instance, a wash at 64° C. could clearly distinguish the Ser$^{29}$ mutants from the wild-type colonies, while the Trp$^{32}$ mutants were detected after two subsequent washes at 62° C. and 63° C. , respectively.

(7) Restriction fragment analysis

Because the Ser$^{29}$ mutation created an Ava2 restriction site and Arg32 destroyed the Ncil restriction site, both corresponding endonucleases could be used for restriction fragment analysis to check once again the presence of the mutation. The colonies were picked up and grown to confluency in 5 ml LB medium containing chloramphenicol. From these cultures, plasmid DNA was prepared, digested with the appropriate restriction endonucleases and electrophoresed on agarose gels, according to classical procedures (Sambrook et al., 1989).

(8) Subcloning to a bacterial expression vector

Figure 1A:
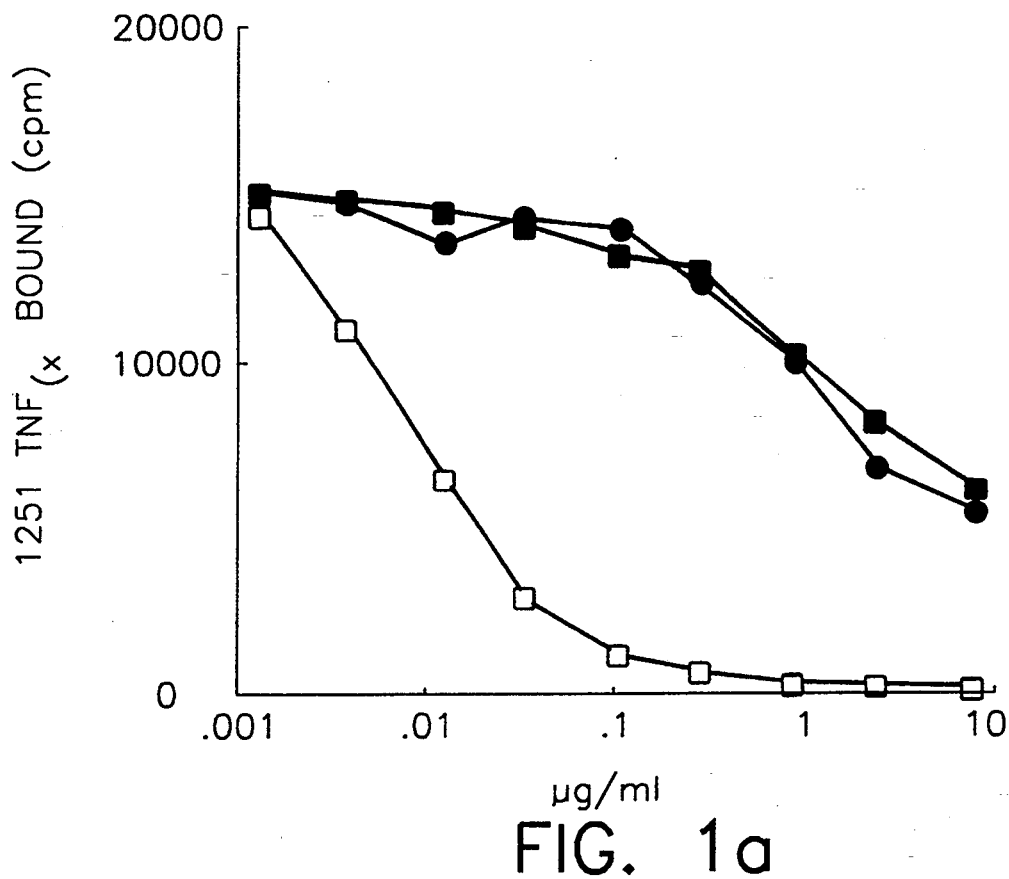
FIG. 1a is a graph showing the results of a competitive binding assay between $^{125}$I-TNF and Trp$^{32}$-TNF, Ser$^{29}$-TNF and wild type-TNF for the p75 receptor.
Figure 1B:
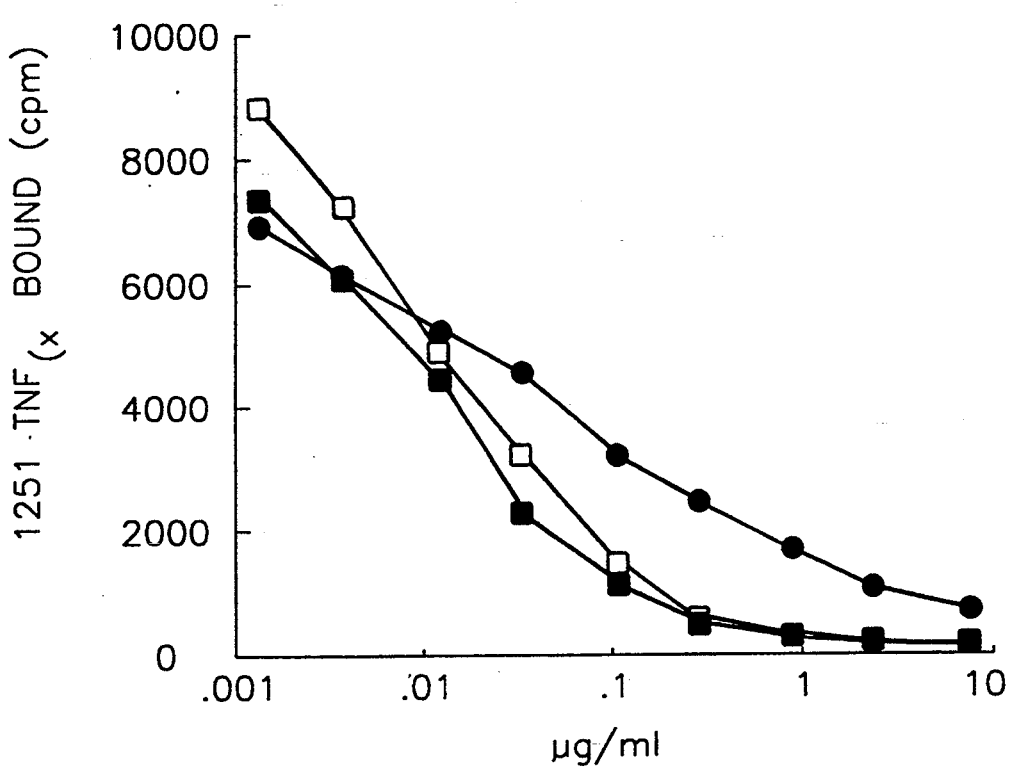
FIG. 1b is a graph showing the results of a competitive binding assay between $^{125}$I-TNF and Trp$^{32}$-TNF, Ser$^{29}$-TNF and wild type-TNF for the p55 receptor.
Figure 2A:
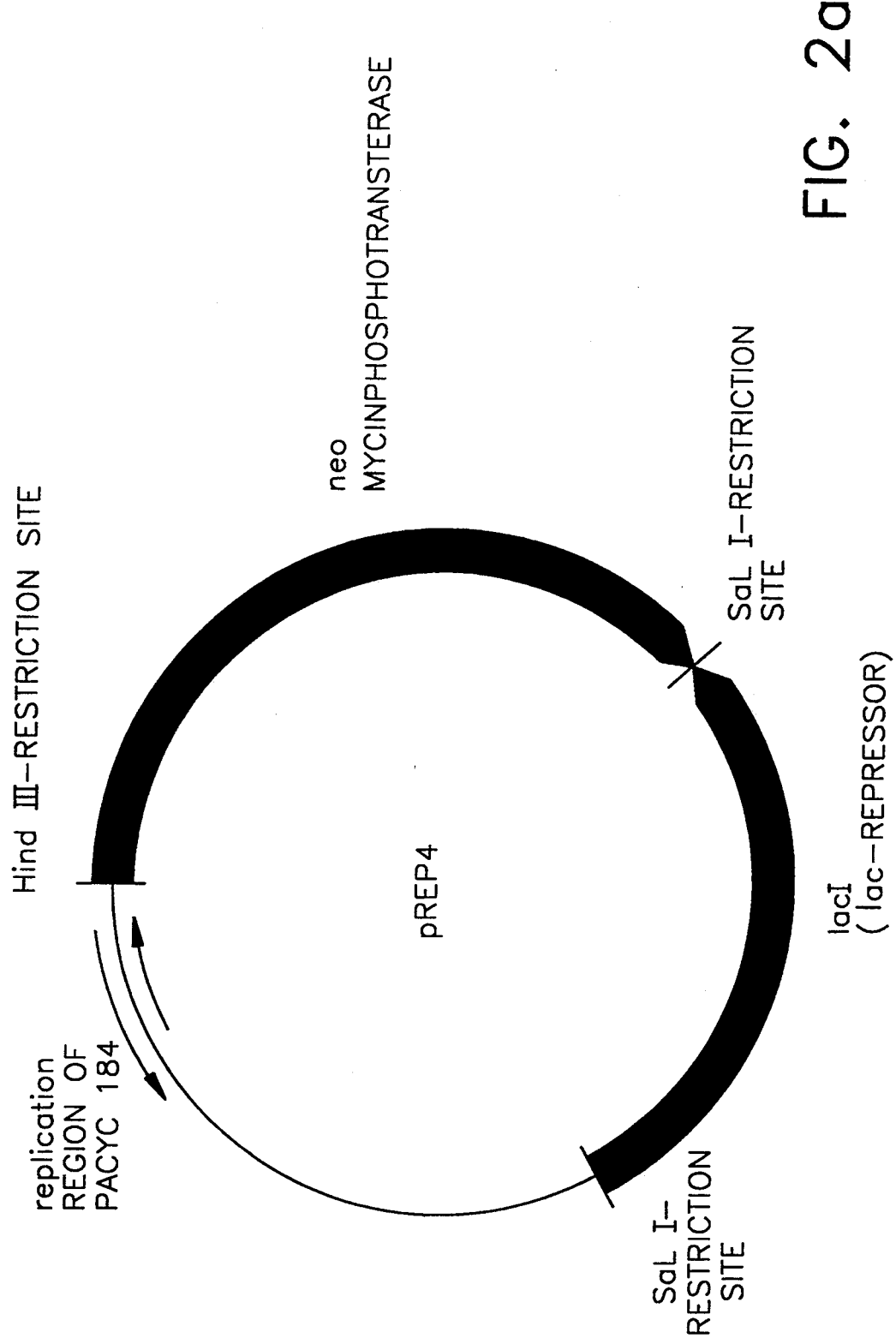
FIG. 2a is a schematic depiction of plasmid pREP4.

Transfer of the mutated TNF gene to an expression vector was carried out exactly the opposite way as the construction of the mutagenesis vector. The phasmid pMc/RBSII,Sph1-TNFα Ser29 or pMc/RBSII,Sph1-TNFα Trp$^{32}$ was digested with EcoR1-HindIII and the small fragment was inserted into the EcoR1-HindIII opened pDS56/RBSII,Sph1-TNFα vector generating plasmids pDS56/RBSII,Sph1-TNFα Ser29 and pDS56/RBSII,Sph1-TNFα Trp32 and transformed into E. coli M15 cells already containing plasmid pREP4 [SEQ ID No: 14] (encoding the lac repressor; see FIGS. 2a and 2b/1–2b/3 for a complete nucleotide sequence of the plasmid given by the one letter standard abreviations for nucleotides) by standard methods. Such cultures of transformed E. coli M15 were grown at 37° C. in LB medium (10 g bacto tryptone, 5 g yeast extract, 5 g NaCI per liter) containing 100 mg/I ampicillin and 25 mg/I kanamycin. At an optical density at 600 nm of about 0.7 to 1.0 units, IPTG s5 was added to a final concentration of 2mM. After an additional 2.5 to 5 h at 37° C. the cells were harvested by centrifugation and the TNF muteins were purified according to Tavernier et al. [J. Mol. Biol. 211, 493–501, (1990)]. The transformed E. coli strains M15 (pREP4;pDS56/R-BSII,Sph1-TNFα Ser29) and M15(pREP4;pDS56/RBSI I,Sph 1 -TNFα Trp32) have been deposited under the Budapest Treaty for patent purposes at the Deutsche Sammlung von Mikroorganismen und Zellkulturen GmbH(DSM) in Braunschweig, BRD at November 19th, 1990 under accession numbers DSM 6240 and DSM 6241 respectively.

Example II

A. Characterization of Ser.$^{29}$-TNFα and Trp$^{32}$-TNFα

1) Differential binding and biogical activity on Hep2and U937 cells (a) Cell culture Hep-2 [ATCC No. CCL 23], U937 [ATCC No. CRL 1593] and RAJI [ATCC No. CCL 86] cells were grown in RPMI 1640 medium, supplemented with 10% (v/v) inactivated fetal calf serum, L-glutamine (2 mM), sodium pyruvate (lmM), 2-mercaptoethanol ($5 \times 10^{-5}$M), 1% of a 100x mixture of non-essential amino acids [Gibro Laboratories, Paisley, GB] and gentamycine (25 mg/ml). The non-adherent cells (U937 and RAJI) were harvested after reaching a density of $1 \times 10^6$ cells/ml. For binding experiments, the adherent Hep-2 cells were grown to confluency, trypsinized, collected and seeded in large Petri dishes (150 cm$^2$) at a density of $2.5 \times 10^6$ cells/mi. Subsequently, the dishes were placed in a CO$_2$-incubator overnight. Because Hep-2 cells are not strongly adherent, the cells could be harvested the same way as the non-adherent cells. Dulbecco's medium, supplemented with 10% inactivated newborn calf serum was used for L929 cell growth.

(b). Determination of the specific activities on L929, Hep-2 and U937 cells.

The amount of protein was determined by the Biorad (Richmond, Calif., USA) protein dye reagent according to the instructions of the manufacturer. The purity of the TNF muteins was determined by SDSPAGE.

The cytotoxic activity on mouse L929 cells was determined using the standard L929 assay (Ruff and Gifford in "Lymphokines", ed. by E. Pick, Vol. 2, 235–275, Academic Press, 1981, Orlando, USA). The cytotoxicity assay on Hep-2 cells was performed the same way as the L929 assay with the only exception that cycloheximide (50 ILg/ml) was added instead of actinomycin D.

(c.) Receptor binding assay.

(i.) -Iodination of TNF-α and Trp$^{32}$-TNF

5 μg Iodogen (Pierce, USA) was dissolved in 10 μl chloroform and dried under a nitrogen stream in a small glass tube. To this, 10 μl Na$^{125}$ 1 (Amersham, 100 mCi/ml in 0.1 M borate buffer, pH 8) was added and kept for 15 min. on ice. This solution was quickly pipetted to an Eppendorf tube, containing 5 μg TNF-α [Pennica et al., s.a.] or 3.2 μg Of Trp$^{32}$-TNF in 10 μl phosphate buffer pH 7. Again the reaction was kept for 15 min on ice. To separate the iodinated TNF-α from the Na$^{125}$, a PD-10 gelfiltration column (Pharmacia) was first equilibrated with 0.1 M phosphate buffer+0.25% gelatin and prerun with 1 μg TNF-α or Trp$^{32}$-TNF, depending on the iodinated TNF species. Subsequently, the reaction mixture was loaded onto the column, and fractions of about 400 μl were collected from which 2 μl aliquots were counted in a γ-counter (LKB 1275 Minigamma, Pharmacia LKB, Uppsala, Sweden). A specific radioactivity of 10–75 and 80 μCi/mg was obtained for TNF-α and Trp$^{32}$-TNF, respectively.

(ii.)-Determination of the $K_D$-value of labeled TNF-α and Trp$^{32}$-TNF by Scatchard analysis A dilution series in multiples of 2 in the range of 12.8nM to 0.006nM of the labeled TNF-α or Trp$^{32}$-TNF was made up in a microtiterplate. Each dilution was made in triplicate. Non-specific binding was measured by the same setup, wherein each point contained a 100 fold excess of unlabeled TNF (1.28 μM to 0.6nM). To each well, approximately 2×10$^6$ cells (U937, Hep-2 or RAJI) were added. The reaction was performed in 0.2 ml tissue culture medium, containing 0.1% NaN$_3$ for 2-3 hours at 4° C. After this, samples were transferred from the microtiterplates to small plastic tubes (Micronic systems), already containing 300 μl phthalate oil (dinonylphthalate 33%, dibutylphthalate 66% (v/v)). The tubes were centrifuged in a microfuge (Eppendorf) for 10 min. to spin down the cells, thereby separating them from the supernatant, using the phthalate oil as a separation medium. After inversion of the tubes, the cell pellet (now on top) could easily be isolated by melting off the top of the tubes with a hot scalpel. The amount of radioactivity, bound on the cells, was measured by counting in a γ-counter. From these data, a Scatchard plot and, subsequently, the dissociation constant $K_D$ was determined using the equilibrium binding type "HOT" in the EBDNLIGAND programm [Mc. Pherson et al., J. Pharmacol. Methods 14, 213–228, (1985)].

(iii)-Determination of the $K_D$ of mutant TNF [Ser$^{29}$-TNF-α and Trp$^{32}$-(iii.)

TNF-α] by competition analysis

The Scatchard data showed that a concentration of 0.4 nM radiolabeled TNF-α was high enough to show a clearly detectable signal and fell within the linear part of the saturation curves. This concentration, however, was also low enough to allow addition up to a 5000 fold excess of cold mutant TNF (2 μM), necessary to perform a competition experiment in which $^{125}$I-wild type TNF is the primary ligand and cold mutant the competitor.

A ten well dilution series of unlabeled mutant TNF (2 mM to 0.004 μM) in concentration steps in mutliples of 2 was set up in a microtiterplate. The two remaining wells contained no unlabeled TNF (total binding) and a 5000 fold excess of the wild-type, unlabeled TNF (background), respectively. To all wells, 0.4 nM of radiolabeled TNF-α (10–75 μCi/μg) was added. After addition of 2×10$^6$ cells, the total volume was 0.2 ml/well. The medium of incubation, reaction conditions and isolation of the cells were exactly the same as described above for the Scatchard analysis experiments. Each point was measured in triplicate and the dissociation experiments were done twice, the average of the two KD's being indicated in Table E. Using the "DRUG" method of the EBDA/LIGAND program, competition curves were plotted and the $K_D$ of the muteins was calculated. The following experimental data were used for such calculations:

1. Labeling of hTNF first labeling (=batch 1):     1.2 × 10$^8$ dpm/5 μg

= 3.7 × 10$^5$ dpm/pmol

= ±10 μCi/μg second labeling (=batch 2:)    5.3 × 10$^8$ dpm/3.2 μg

= 1.9 × 10$^6$ dpm/pmol

= ±75 Ci/μg

2. Determination of the $K_D$ of wild-type TNF

We measured the $K_D$ of $^{125}$I-TNF (batch 1) on Hep-2 and U937 cells by Scatchard analysis.

Hep-2: $K_D = 9.17 \times 10^{-10}$

U937: $K_D = 2.5 \times 10^{-10}$

3. Competition experiments

All displacement experiments were carried out, using $^{125}$I-TNF (batch 1) as the primary ligand, except experiment B.3 (table B, 3.), where $^{125}$I-TNF (batch 2) was used.

In each experiment, the binding at each concentration was measured in triplicate and only the averages are shown in the following tables (A-D).

From each experiment shown in these tables, the $K_D$ value was calculated using the programm of Mc. Pherson et al. (1985). The average of the $K_D$ determinations (2 experiments for Ser$^{29}$-TNFα on Hep-2 cells and on U937 cells, two experiments for Trp$^{32}$-TNFα on Hep-2 cells and three on U937 cells) are shown in table E.

TABLE A

Competition with Ser$^{29}$-TNFα on U937 cells.

| Mean dpm | concentration of mutant [mol] |
|---|---|
| 1. 2120 | 0 |
| 1869 | 1 × 10$^{-9}$ |
| 1779 | 2 × 10$^{-9}$ |
| 1719 | 4 × 10$^{-9}$ |
| 1708 | 8 × 10$^{-9}$ |
| 1575 | 1.6 × 10$^{-8}$ |

TABLE A-continued

Competition with Ser$^{29}$-TNFα on U937 cells.

| | Mean dpm | concentration of mutant [mol] |
|---|---|---|
| | 1415 | $3.2 \times 10^{-8}$ |
| | 1320 | $6.4 \times 10^{-8}$ |
| | 1200 | $1.25 \times 10^{-7}$ |
| | 983 | $2.5 \times 10^{-7}$ |
| | 949 | $5 \times 10^{-7}$ |
| | 632 | $1 \times 10^{-6}$ |
| | 533 | $2 \times 10^{-6}$ |
| Background: | 299 | |
| 2. | 1014 | 0 |
| | 635 | $4 \times 10^{-9}$ |
| | 603 | $8 \times 10^{-9}$ |
| | 641 | $1.5 \times 10^{-8}$ |
| | 572 | $3 \times 10^{-8}$ |
| | 489 | $6 \times 10^{-8}$ |
| | 413 | $1.2 \times 10^{-7}$ |
| | 380 | $2.5 \times 10^{-7}$ |
| | 319 | $5 \times 10^{-7}$ |
| | 263 | $1 \times 10^{-6}$ |
| | 238 | $2 \times 10^{-6}$ |
| Background: | 205 | |

TABLE B

Competition with Trp$^{32}$-TNF-α on U937 cells

| | | |
|---|---|---|
| 1. | 2120 | 0 |
| | 1917 | $1 \times 10^{-9}$ |
| | 1698 | $2 \times 10^{-9}$ |
| | 1655 | $4 \times 10^{-9}$ |
| | 1585 | $8 \times 10^{-9}$ |
| | 1488 | $1.5 \times 10^{-8}$ |
| | 1377 | $3 \times 10^{-8}$ |
| | 1333 | $6 \times 10^{-8}$ |
| | 1166 | $1.25 \times 10^{-7}$ |
| | 1026 | $2.5 \times 10^{-7}$ |
| | 953 | $5 \times 10^{-7}$ |
| | 777 | $1 \times 10^{-6}$ |
| | 628 | $2 \times 10^{-6}$ |
| Background: | 299 | |
| 2. | 1047 | 0 |
| | 653 | $4 \times 10^{9}$ |
| | 629 | $8 \times 10^{-9}$ |
| | 636 | $1.5 \times 10^{-8}$ |
| | 585 | $3 \times 10^{-8}$ |
| | 546 | $6 \times 10^{-8}$ |
| | 508 | $1.2 \times 10^{-7}$ |
| | 479 | $2.5 \times 10^{-7}$ |
| | 422 | $5 \times 10^{-7}$ |
| | 357 | $1.10^{-6}$ |
| | 294 | $2 \times 10^{-6}$ |
| Background: | 214 | |
| 3. | 8340 | 0 |
| (carried out | 4759 | $4 \times 10^{-9}$ |
| with $^{125}$I- | 4041 | $8 \times 10^{-9}$ |
| TNF, batch 2) | 3620 | $1.5 \times 10^{-8}$ |
| | 3275 | $3 \times 10^{-8}$ |
| | 3034 | $6 \times 10^{-8}$ |
| | 2387 | $1.25 \times 10^{-7}$ |
| | 1981 | $2.5 \times 10^{-7}$ |
| | 1472 | $5 \times 10^{-7}$ |
| | 1192 | $1 \times 10^{-6}$ |
| | 814 | $2 \times 10^{-6}$ |
| Background: | 307 | |

TABLE C

Competition with Ser$^{29}$-TNF-α on Hep-2 cells

| | | |
|---|---|---|
| 1. | 938 | 0 |
| | 799 | $1 \times 10^{-9}$ |
| | 677 | $2 \times 10^{-9}$ |
| | 564 | $4 \times 10^{-9}$ |
| | 510 | $8 \times 10^{-9}$ |
| | 451 | $1.6 \times 10^{-8}$ |
| | 442 | $3.2 \times 10^{-8}$ |
| | 446 | $6.4 \times 10^{-8}$ |
| | 379 | $1.25 \times 10^{-7}$ |

TABLE C-continued

Competition with Ser$^{29}$-TNF-α on Hep-2 cells

| | | |
|---|---|---|
| | 374 | $2.5 \times 10^{-7}$ |
| | 437 | $5 \times 10^{-7}$ |
| | 359 | $1 \times 10^{-6}$ |
| | 383 | $2 \times 10^{-6}$ |
| Background: | 353 | |
| 2. | 457 | 0 |
| | 273 | $4 \times 10^{-9}$ |
| | 240 | $8 \times 10^{-9}$ |
| | 253 | $1.5 \times 10^{-8}$ |
| | 235 | $3 \times 10^{-8}$ |
| | 207 | $6 \times 10^{-8}$ |
| | 239 | $1.2 \times 10^{-7}$ |
| | 215 | $2.5 \times 10^{-7}$ |
| | 211 | $5 \times 10^{-7}$ |
| | 193 | $1 \times 10^{-6}$ |
| | 238 | $2 \times 10^{-6}$ |
| Background: | 215 | |

TABLE D

Competition with Trp$^{32}$-TNF-α on Hep-2 cells

| | | |
|---|---|---|
| 1. | 938 | 0 |
| | 742 | $1 \times 10^{-9}$ |
| | 608 | $2 \times 10^{-9}$ |
| | 537 | $4 \times 10^{-9}$ |
| | 547 | $8 \times 10^{-9}$ |
| | 397 | $1.6 \times 10^{-8}$ |
| | 394 | $3.2 \times 10^{-8}$ |
| | 405 | $6.4 \times 10^{-8}$ |
| | 395 | $1.25 \times 10^{-7}$ |
| | 388 | $2.5 \times 10^{-7}$ |
| | 379 | $5 \times 10^{-7}$ |
| | 353 | $1 \times 10^{-6}$ |
| | 386 | $2 \times 10^{-6}$ |
| Background: | 353 | |
| 2. | 445 | 0 |
| | 298 | $4 \times 10^{-9}$ |
| | 222 | $8 \times 10^{-9}$ |
| | 256 | $1.5 \times 10^{-8}$ |
| | 202 | $3 \times 10^{-8}$ |
| | 227 | $6 \times 10^{-8}$ |
| | 210 | $1.2 \times 10^{-7}$ |
| | 221 | $2.5 \times 10^{-7}$ |
| | 197 | $5 \times 10^{-7}$ |
| | 231 | $1 \times 10^{-6}$ |
| | 202 | $2 \times 10^{-6}$ |
| Background: | 203 | |

TABLE E

| | Hep-2 | | U937 | L929 |
|---|---|---|---|---|
| | affinity ($K_D$) | specific activity (U/mg) | affinity ($K_D$) | specific activity (U/mg) |
| TNF-α | $9.17 \times 10^{-10}$(*) (100%) | $2.9 \times 10^7$ (100%) | $2.5 \times 10^{-10}$(*) (100%) | $2 \times 10^7$ (100%) |
| Ser$^{29}$-TNF-α | $1.06 \times 10^{-9}$ (86.5%) | $9.3 \times 10^6$ (32%) | $5.07 \times 10^{-8}$ (0.49%) | $10^5$ (0.5%) |
| Trp$^{32}$-TNF-α | $1.06 \times 10^{-9}$ (86.5%) | $4.5 \times 10^7$ (155%) | $3.53 \times 10^{-8}$ (0.71%) | $6.4 \times 10^4$ (0.32%) |

$K_D$ values indicated by an asterisk (*) were obtained by Scatchard analysis. All other $K_D$ values were determined by competition analysis. Relative values (in percentage to TNF-α) are indicated between brackets.

It can be seen that the binding constant ($K_D$) of Ser$^{29}$-TNF-α and Trp$^{32}$-TNF-α determined with Hep-2 cells (which only carry the p55-TNF-R) are almost the same as TNF-α. Also the biological activity (specific activity) on these cells is largely retained (note that the accuracy of this assay is only a factor of 3). Strikingly, the binding affinity (measured in the competition assay) of Ser$^{29}$-TNF-α and Trp$^{32}$-TNF-α to the U937 cells, which predominantly but not exclusively, carry the high affinity receptor p75-TNF-R, has been largely lost (increase in $K_D$-value by a factor of more than 100). Thus, the binding affinity of the Ser$^{29}$-TNF-a for p75-TNF-R has been reduced approximately 50 fold to about 2% of its binding affinity to p55-TNF-R. The binding affinity of Trp$^{32}$-TNF-$\alpha$ for p75-TNF-R has been reduced approximately 33 fold to about 3% of its binding affinity to p55-TNF-R. It may also be noted that the biological activity of Ser$^{29}$-TNF-$\alpha$ and Trp$^{32}$-TNF-$\alpha$, determined in the standard assay based on L929-cells, has been largely lost (decrease by a factor more than 100).

Differential binding to the human p75-TNF-R and the human p55-TNF-R

Competition of human $^{125}$l-TNF-$\alpha$ binding by Trp$^{32}$- and Ser$^{29}$-TNF-$\alpha$ and human TNF-$\alpha$ to TNF-receptors purified from HL60 cells was determined as follows. 2 $\beta$l aliquots of the native p55-TNF-R and the p75-TNF-R purified as described in European Patent Application No. 90116707.2 dissolved at a concentration of about 0.3 $\mu$g/ml in 20 mM Hepes, 50 mM Tris, 50 mM NaCl, 1 mM EDTA, 0.1% octylglucoside, 0.1 mg/ml BSA, pH 8.0, were spotted onto prewetted nitrocellulose filters in triplicate. The filters were blocked with blocking buffer (50 mM Tris, 140 mM NaCl, 5 mM EDTA, 0.02% $NaN_3$, 1% defatted milk powder) for 1.5 hours at room temperature. After washing with PBS the filters were incubated with 10 ng/ml $^{125}$l-TNF$\alpha$ and varying concentrations of Trp$^{32}$-or Ser$^{29}$-TNF$\alpha$, or TNF$\alpha$ overnight at 4° C. . The filters were washed with blocking buffer (2x for 5 min.) and with $H_2O$ (1x for 5 min.), air dried, and counted in a $\gamma$-counter. Results are given in FIGS. 1*a* and *b*, whereby FIG. 1 shows binding of TNF$\alpha$ (open rectangle), Ser$^{29}$-TNF$\alpha$ (filled circles) and Trp$^{32}$-TNF$\alpha$ (filled rectangle) to human p75TNF-R in case of FIG. 1*a* to human p75-TNF-R and in case of FIG. 1*b* to human p55-TNF-R. Based on the data shown in FIG. 1 and in addition those of FIG. 7 the IC50-values were calculated and are listed for Ser$^{29}$- and Trp$^{32}$-TNF$\alpha$ in Table F. Values for the decrease in affinity for these muteins on both receptors with respect to TNF$\alpha$ are also given in Table F. Values for "S", the selectivity factor, based on IC50 values given in Table F and calculated from FIG. 7 are shown in Table G.

TABLE F

| Receptor | Competitor | IC50 $\mu$g/ml | Decrease in Affinity |
|---|---|---|---|
| p75-TNF-R | TNF$\alpha$ | 0.010 | — |
| | Ser$^{29}$-TNF$\alpha$ | 2.5 | 250 |
| | Trp$^{32}$-TNF$\alpha$ | 5 | 500 |
| p55-TNF-R | TNF$\alpha$ | 0.011 | — |
| | Ser$^{29}$-TNF$\alpha$ | 0.09 | 8.2 |
| | Trp$^{32}$-TNF$\alpha$ | 0.017 | 1.5 |

TABLE G

| Mutein | $S = \frac{\text{IC50 p75-TNF-R}}{\text{IC50 p55-TNF-R}}$ |
|---|---|
| TNF$\alpha$ | 1 |
| Ser$^{29}$-TNF$\alpha$ | 28 |
| Trp$^{32}$-TNF$\alpha$ | 294 |
| Gly$^{29}$-TNF$\alpha$ | 80 |
| Tyr$^{29}$-TNF$\alpha$ | 110 |
| Tyr$^{32}$-TNF$\alpha$ | 90 |
| Ser$^{29}$-Trp$^{32}$-TNF$\alpha$ | 450 |

Example III

Purification of Tr$^{32}$-TNF$\alpha$

Transformed cells obtained according to Example I were processed in the following manner:

a) Opening by French press, addition of polyethyleneimine until a final concentration of 0.4%, pH 7.6; and removal of precipitate.

b) Ammonium sulphate precipitation at pH 7.2; fraction 30–70% c) Dialysis against 25% ammonium sulphate in 10 mM Tris, pH 6.8 d) Phenyl-Sepharose column CL-4B (35×250 mm) Load in 25% ammonium sulphate - 10 mM Tris, pH 6.8

Elution: gradient 25% ammonium sulphate-Tris buffer to 20 mM ethanolamine, pH 9 (2 times 150 ml).

e) Column Mono Q (HR 16/10). Load: in 20 mM ethanolamine, pH 9. Elution: gradient (2 times 300 ml) in the same buffer, from 0 to 1 M sodium chloride (Pharmacia, FPLC). Active fractions dialysed versus 0.01 M phosphate buffer pH 7 f) Column of Heparin Sepharose CL-6B (30×80 mm) Load in 0.01 M phosphate buffer pH 7. Elute with a gradient in the same buffer from 0 to 1 M sodium chloride g) Active fractions were concentrated on Amicon (micro-ultrafiltration system 8 MC; membrane ©25 mm; diaflo 10 YM10 - 25 mm) and separately loaded on a gelfiltration column (Ultrapac TSK G-2000 SWG; 21.5×600 mm), equilibrated in 0.01 M phosphate pH 7 and 0.9% sodium chloride LPS (determined by test kit of Kabivitrum):

Most active fraction contained 5 mg/ml Trp$^{32}$-TNF$\alpha$; endotoxin content: 26 E.U./mg The last active fraction contained 1.8 mg/ml TNF and 47 E.U./mg protein.

Example IV.

Anti-tumour effect of hTNF$\alpha$ and hIFN$\gamma$ on subgutaneous HT-29 tumours in nude mice.

5×10$^6$ HT-29 human colon adenocarcinoma cells [ATCC HTB38] were subcutaneously injected in nude mice. Groups consisted of 5 mice. The treatment comprises daily perilesional injections during 6 days per week, followed by 1 day without treatment. Results are given in FIG. 4 whereby "PBS" refers to phosphate buffered saline as known in the art. The single arrow indicates the start of the treatment with 5 $\mu$g hTNF$\alpha$ or 5000 IU human Interferon $\gamma$ (hIFN$\gamma$) or both. The double arrow indicates the time that these doses were doubled and the crossed arrow indicates the end of the treatment.

2. Comparison of the anti-tumour potential of hTNF$\alpha$ and Trp$^{32}$- TNF$\alpha$ 5×10$^6$ HT-29 human colon adenocarcinoma cells were subcutaneously injected in nude mice. Groups consisted of 5 mice. The treatment started on day 6 following inoculation and comprises daily perilesional injections during 6 days per week. Tumour volume was estimated every 3 or 4 days by measuring the larger (a) and the smaller (b) diameter and calculating the a×b$^2$×0.4 according to Attia and Weiss as known in the art. Results are given in FIG. 5 whereby the arrow indicates the start of the treatment and open triangles with tip down refers to 10$^4$ IU of hIFN$\gamma$ and 10 $\mu$g hTNF$\alpha$, filled triangles with tip down refer to 10$^4$ IU of hIFN$\gamma$ and 10 $\mu$g Trp$^{32}$-TNF, filled rectangles refer to 10 $\mu$g Trp$^{32}$-TNF$\alpha$, open reactangles refer to 10 $\mu$g hTNF$\alpha$, open triangles refer to phosphate buffered saline and filled circles refer to $10^4$ IU of hIFNγ. In vitro, there is no difference in cytotoxicity for Hep or HT-29 cells between hTNFα and $Trp^{32}$-TNFα.

EXAMPLE V

Preparation of $Ser^{29}$-Trp$D^{32}$-TNFα

$Ser^{29}$-$Trp^{32}$-TNFα was prepared as described in Example I with the following exceptions:

1. The oligonucleotide used, contains the following sequence [SEQ ID No: 17] (mutated bases underlined):
5'GGGCATTGGCCCAGCGGTTGGACCACT-GGAGC3'
2. An Nci 1site was destroyed while an Ava 2-site was created, allowing for check of the presence of the mutation by restriction fragment analysis. No hybridization analysis was performed. 6 clones resulting from the WK6 transformation were grown up and DNA was prepared and analysed as described in Example I, 3 of the 6 clones contained the mutation.

This DNA sequence was subcloned into the pDS56 expression vector, generating the plasmid pDS56/RBSII,Sph1-TNFαSer29Trp32, and transformed to the *E. coli* M15 strain. Expression and purification was performed as described in Example 1.

EXAMPLE VI

Preparation of $Gly^{29}$-TNFα, $Tyr^{29}$-TNFα and $Tyr^{32}$-TNFα

$Gly^{29}$-TNFα, $Tyr^{29}$-TNFα and $Tyr^{32}$-TNFα were prepared as described in Example I with the following exception. Oligonucleotides were used, containing a fully degenerated codon at position 29 or 32, resulting in a random insertion of all twenty amino acids at one of the two positions. The sequence of these oligonucleotides are as follows:

Position 29 [SEQ ID No: 18]
5'CCACGCCATTCGCGAGGAGG-GCATTGGCCCGGCGGTNNNCCACT-GGAGC3'

Position 32 [SEQ ID No:19]:
5'CCACGCCATTCGCGAGGAGG-GCATTGGCNNNGCGGTTCAGCC3' where N=A, C, G or T and mutated bases are underlined.

Figure 4:
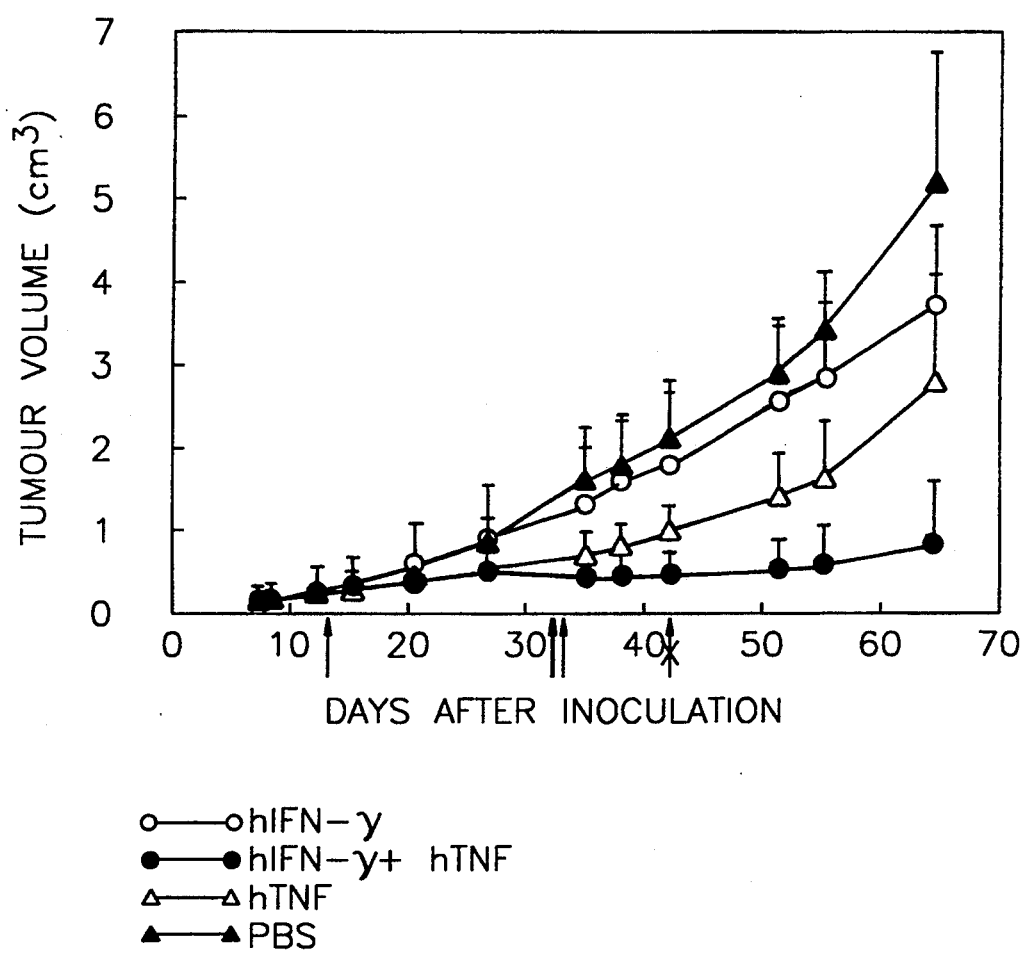
FIG. 4 is a graph showing the results of an assay measuring the antitumor effect of interferon-gamma and TNF, alone or in combination.
Figure 5:
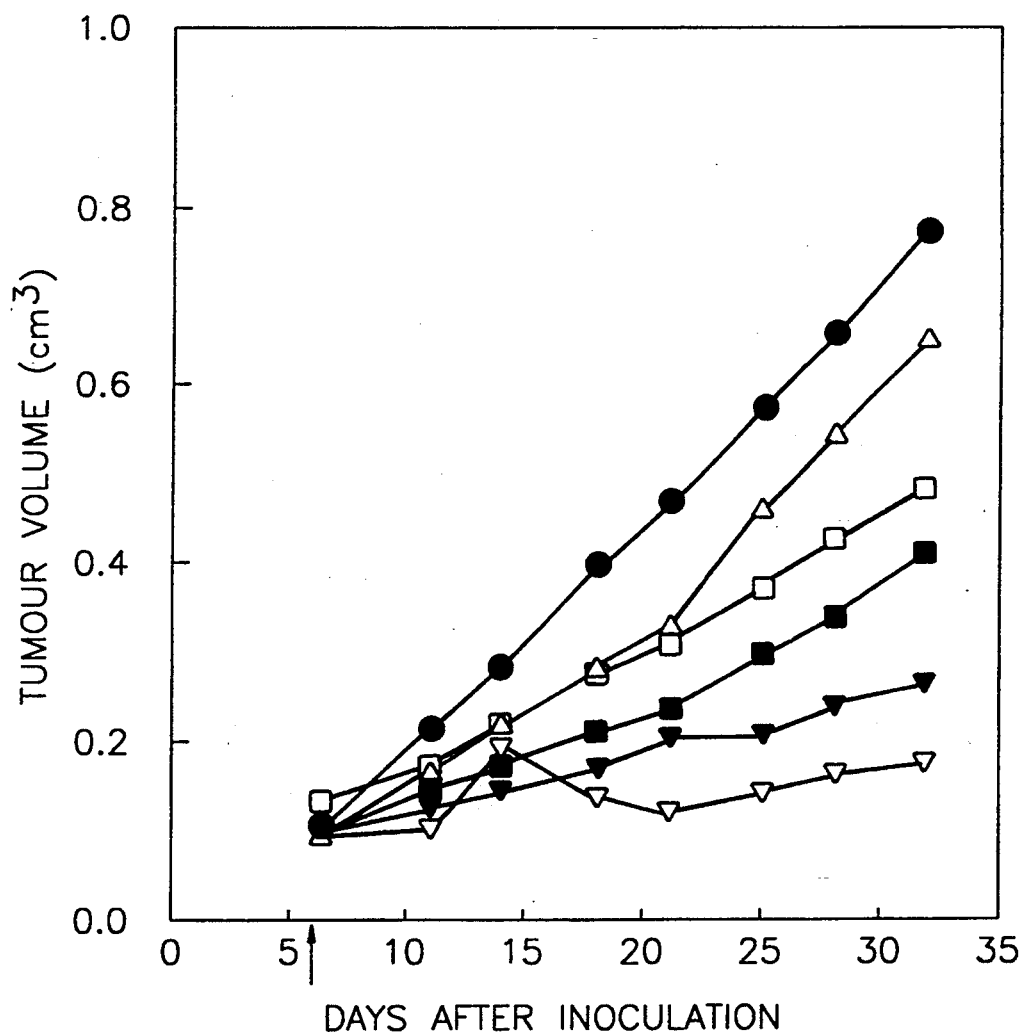
FIG. 5 is a graph showing the results of an assay measuring the antitumor effect of interferon-gamma and TNF, alone or in combination and Trp$^{32}$-TNF alone or in combination with interferongamma.

Together with the mutation, also a unique Nru-1 site is introduced. Thus, instead of directly transforming the phasmid-pool, isolated from o the WK6 muts strain, this DNA was first digested with Nru-1, the linear band eluted from the agarose gel, ligated and transformed to the SURE strain (Stratagene, La Jolla, Calif., USA). In this way, one can select only for phasmids, containing the mutations. 168 colonies obtained were inoculated in microtiterplates, grown to confluency and their lysates tested for biological activity towards Hep-2 cells in a manner as described in Example IIa and for differential binding as described in Example IIb or Example VIII. On the basis of the biological activity on the one side and differential binding as determined according to Example IIB or Example VIII colonies were selected and further characterized by DNA sequence analysis of corresponding inserts as known in the art. DNAsequences coding for $Gly^{29}$-TNFα, $Tyr^{29}$-TNFα and $Tyr^{32}$-TNFα were isolated from corresponding colonies and cloned in bacterial expression vectors as described in Example I. Muteins expressed were purified to more than 95% homogeneity by means of a MONO-Q ion exchange chromatography step.

EXAMPLE VII

Preparation of $Glu^{31}$-TNFα and $Asn^{31}$-$Thr^{32}$-TNFα

Mutagenesis of the TNFα gene using PCR

Three PCR reactions were performed with plasmid pDS56/RBSII,Sph1-TNFα [SEQ ID No:2][FIG. 3] as the template DNA using a Perkin-Elmer Cetus GeneAmp ™ DNA Amplification Reagent Kit with AmpliTaq ™ Recombinant Taq DNA Polymerase (Perkin Elmer Cetus, Vaterstetten, BRD) [see FIG. 8]. In reaction I primers 17/F [SEQ ID No: 20](5'-GGCGTATCACGAGGCCCTTTCG3'; primer 17/F comprises nucleotides 3949–3970 of plasmid pDS56/RBSII,SphI-TNFα) and 21/M5 [SEQ ID No: 22] (5-ATTGGCCCGCTCGTTCAGCCACT-GGAGCTGCCCCTC-3'; primer 21/M5 comprises nucleotides which are complementary to nucleotides 219–184 of plasmid pDS56/RBSII,Sph1-TNFα, mutated bases are underlined) were used, reaction II contained primers 17/F and 21/M6 [SEQ ID No:23] (5'-ATTGGCAGTGTTGTTCAGCCACTGGAG-CTGCCCCTC-3'; primer 21/M6 comprises nucleotides which are complementary to nucleotides 219–184 of plasmid pDS56/RBSII,Sph1-TNFα, mutated bases are underlined), and reaction III contained primers 21/MR [SEQ ID No: 24] (5'-GCCCTCCTGGCCAATGGCGTGG-3'; primer 21/MR comprises nucleotides 220–241 of plasmid pDS56/RBSII,Sph1-TNFα) and 17/O [SEQ ID No: 21] (5'-CATTACTGGATCTATCAACAGG-3'; primer 17/O comprises nucleotides which are complementary to nucleotides 748–727 of plasmid pDS56/RBSII,Sph1-TNFα). Therfore 10 μl template DNA (10 g), 5 μl each of the two primers (100 pmole each), 16 μl dNTP's mix (1.25 mM of dATP, dGTP, dCTP, and dTTP), 10 μl 10x reaction buffer (100 mM Tris-HCl pH8.3, 500 mM KCL, 15 mM $MgCl_2$ and 0.1% gelatin), 1 μl (5 units) AmpliTaq ™ DNA polymerase and 53 μl $H_2O$ were mixed in an Eppendorf tube and overlaid with 80 μl mineral oil (Perkin-Elmer Cetus). The tubes were transferred to a DNA thermal cycler (TRIO-Thermoblock, Biometra) and kept for 1 min at 94°0 C., before 35 cycles of melting the DNA (1 min at 94° C.), annealing the primers (1 min at 50° C.), and extending the primers (3 min at 72°0 C.) were performed. After additional 2 min at 72° C., the reactions were cooled to room temperature and extracted with chloroform. The DNA present in the aqueous phase was precipitated with ethanol and subjected to electrophoresis in a 6 polyacrylamide gel [Sambrook et al., 1989]. After staining of the DNA with ethidium bromide, fragments I, II and III [see FIG. 8; these fragments originate from reactions I, II and III, respectively] were isolated from the gel and purified [Sambrook et al., 1989].

Preparation of DNA fragments encoding $Glu^{31}$-TNFα and $Asn^{31}$-$Thr^{32}$-TNFα

Fragments I, II and III were enzymatically phosphorylated, before in two parallel reactions fragments I and III and fragments II and III were ligated with each other [Sambrook et al., 1989]. After heat-inactivation of the ligase and digestion with restriction enzymes EcoRI and HindIII, the DNA was subjected to electrophoresis in a 6% polyacrylamide gel. After staining of the DNA with ethidium bromide, the EcoRI-HindIII fragments A and B [see FIG. 4] were isolated from the gel and purified as previously described.

Preparation of plasmids encoding Glu$^{31}$-TNFα and Asn$^{31}$-Thr$^{32}$-TNFα

In separate experiments, the EcoRI-HindIII fragments A and B were inserted according to standard methods [Sambrook et al., 1989] into the EcoRI-HindIII opened plasmid pDS56/RBSII,Sph1-TNFαSer29 generating plasmids pDS56/RBSII,Sph1-TNFαGlu31 and pDS56/RBSII,Sph1TNFαAsn31Thr32, respectively. Plasmid DNA was prepared [Birnboim et al., 1979] and the identity of the coding region for the TNFα muteins was confirmed by sequencing the double-stranded DNA [Sambrook et al., 1989].

Production of Glu$^{31}$-TNFα and Asn$^{31}$-Thr$^{32}$-TNFα

Plasmids pDS56/RBSII,Sph1-TNFαGlu31 and pDS56/RBSII,Sph1TNFαAsn31Thru32 were transformed into E. coli M15 cells containing already plasmid pREP4 by standard methods. Transformed cells were grown at 37° C. in LB medium containing 100 mg/l ampicillin and 25 mg/l kanamycin. At an optical density at 600 nm of about 0.7 to 1.0, IPTG was added to a final concentration of 2 mM. After additional 2.5 to 5 h at 37° C. the cells were harvested by centrifugation.

EXAMPLE VIII

Differential binding recombinant human p75-TNF-R and recombinant human p55-TNF-R 1. 10 ml suspensions of transformed and induced E. coli cells expressing recombinant human TNFα, Ser$^{29}$-TNFα, Trp$^{32}$-TNFα, Glu$^{31}$-TNFα, and Asn$^{31}$-Thr$^{32}$-TNFα [E. coli cells expressing recombinant dihydrofolate reductase (DHFR) were included as a control] were centrifuged at 4,000 rpm for 10 min and resuspended in 0.9 ml of lysis buffer (10 mM Tris-HCl pH 8.0, 5 mM EDTA, 2 mM PMSF, 10 mM benzamidine, 200 units/ml aprotinine and 0.1 mg/ml lysozyme). After 20 min incubation at room temperature 50 μl of 1M MgCl$_2$, 20 μl of 5 mg/ml DNaseI, 50 μl of 5M NaCl and 50 μl of 10% NP-40 were added and the mixture was further incubated at room temperature for 15 min. 0.5 ml of the lysate clarified by centrifugation at 13,000 rpm for 5 min was subjected to ammonium sulfate precipitation (30%–70% cut). The 70% ammonium sulfate pellet was dissolved in 0.2 ml PBS and analyzed by SDS-PAGE to confirm the presence of the recombinant proteins.

Figure 6E:
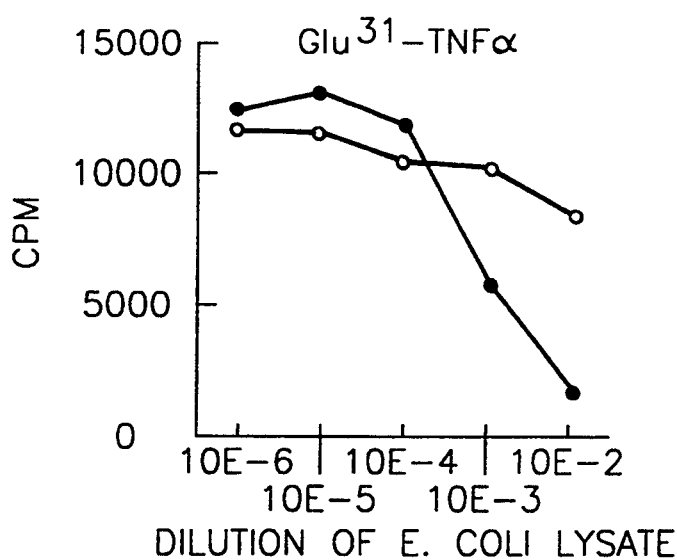
FIG. 6 is a series of graphes showing the results of a competitive binding assay between $^{125}$I-TNF and various muteins for the p75 receptor and the p55 receptor.
Figure 6F:
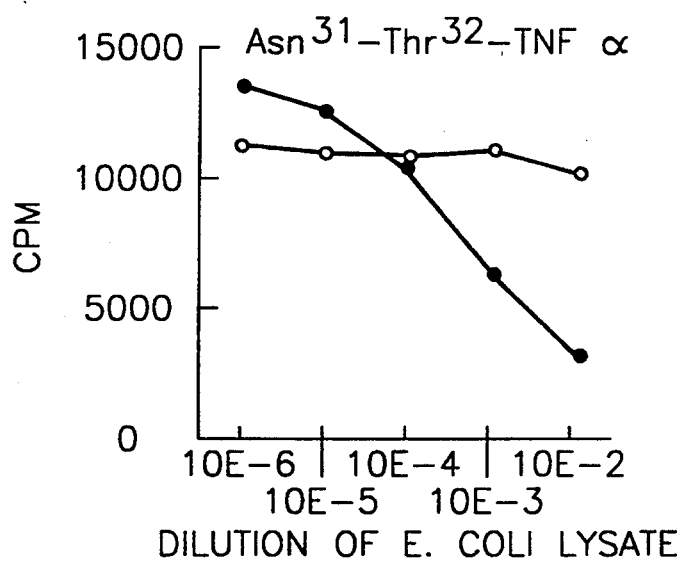
Figure 7A:
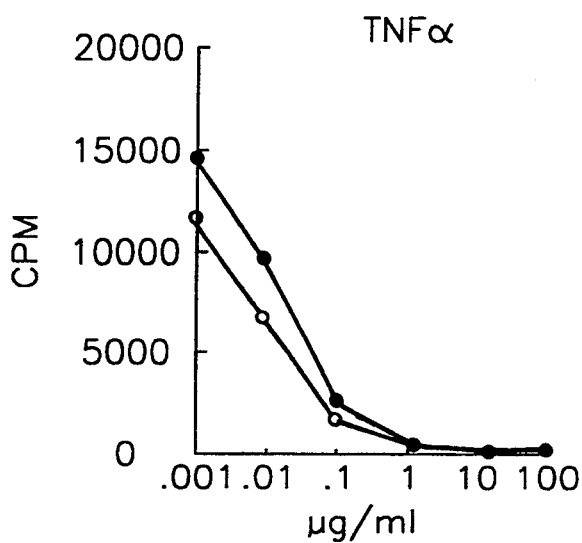
FIG. 7 is a series of graphs showing the results of a competitive binding assay between $^{125}$I-TNF and various muteins for the p75 receptor and the p55 receptor.
Figure 7B:
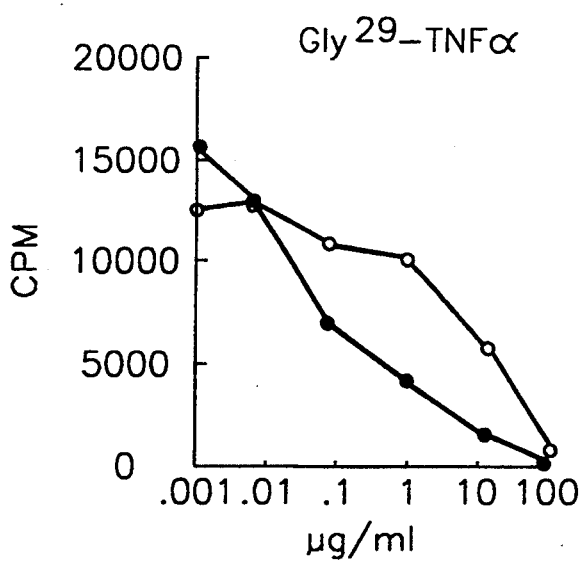
Figure 7C:
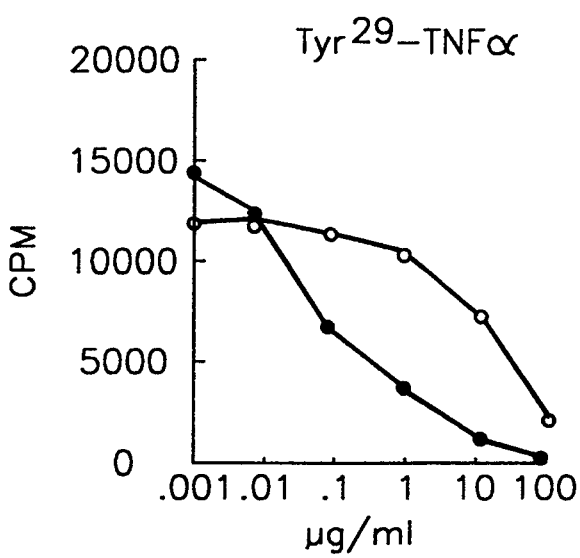
Figure 7D:
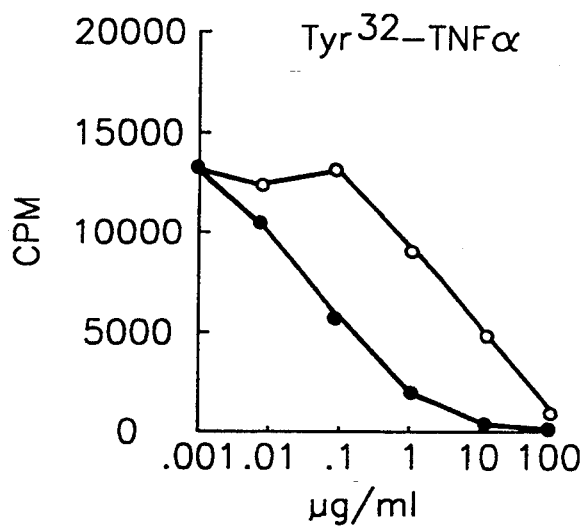
Figure 7E:
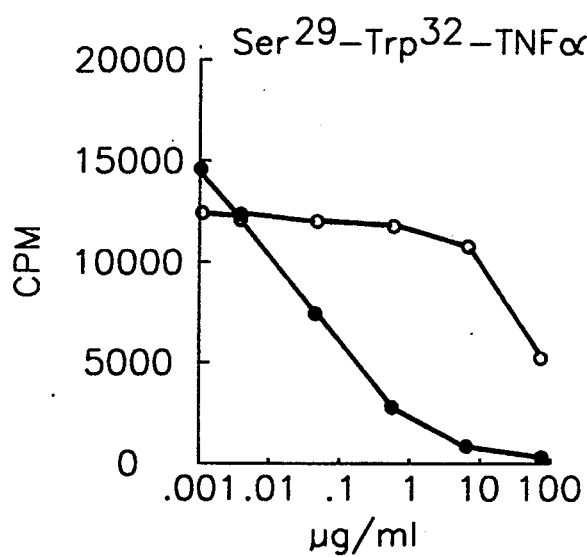
Figure 8:
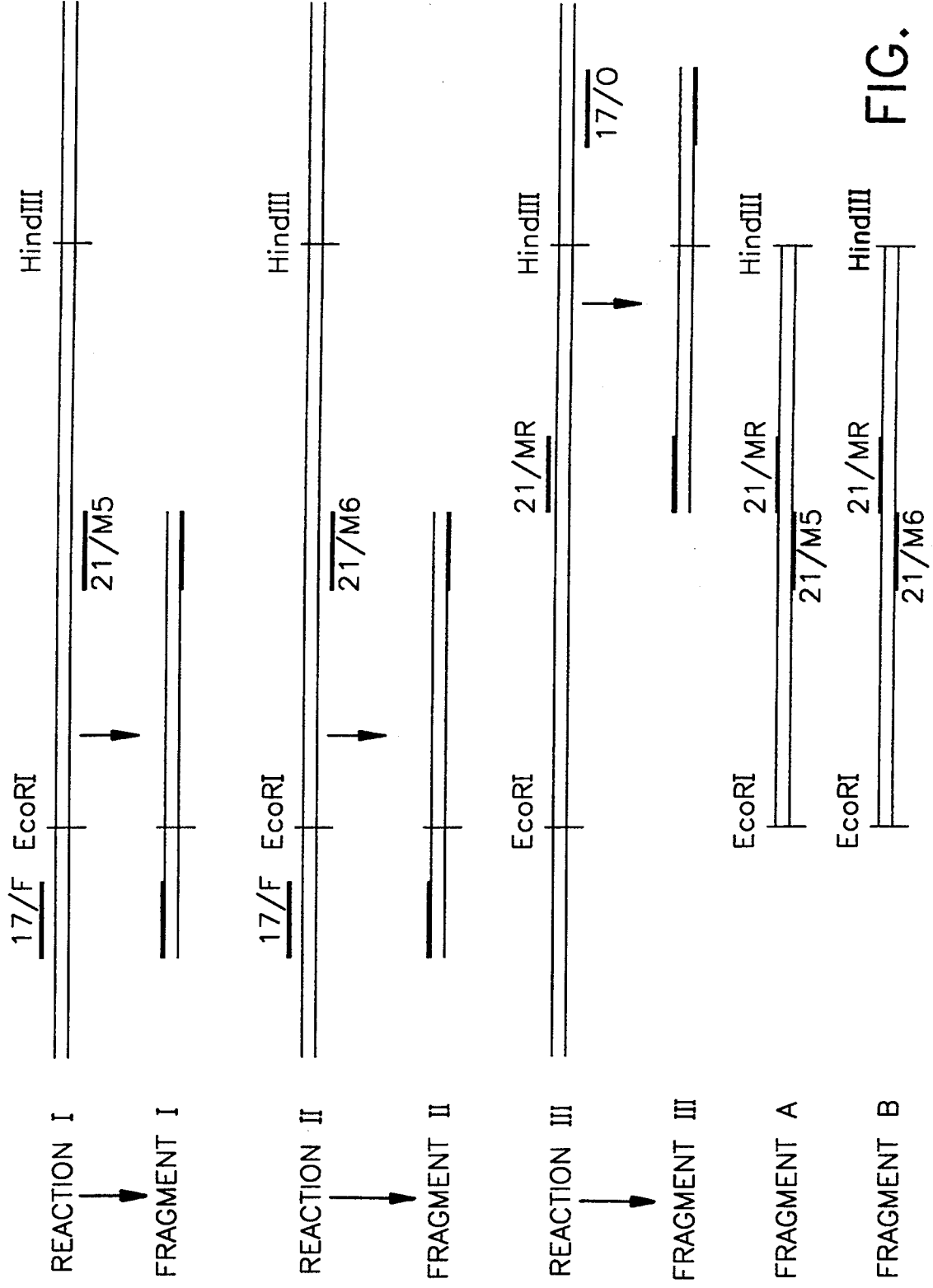
FIG. 8 is a schematic representation of mutagenesis of the TNF β gene using PCR with primers containing the altered codons.

For the differential binding assay microtiter plates were coated with recombinant human p75-TNF-R-human IgGγ3 and p55-TNF-R-human IgGγ3 fusion proteins (European Patent Applications Publ. Nos. 417 563, 422 339) dissolved in PBS at 0.3 μg/ml and 0.1 μg/ml, respectively, (100 μl/well, overnight at 4° C.). After blocking with blocking buffer (50 mM Tris pH 7.4, 140 mM NaCl, 5 mM EDTA, 0.02% NaN$_3$, 1% defatted milk powder) the microtiter plate was washed with PBS and incubated with 5 ng/ml human $^{125}$I-TNFα (labelled by the Iodogen method to a specific activity of about 30 μCi/μg as described above) in the presence of different dilutions of the E. coli lysate partially purified by ammonium sulfate precipitation. The volume was 100 μl/well and each dilution was assayed in duplicate. After three hours at room temperature the wells were thoroughly washed with PBS and counted in a γ-counter. Results are shown in FIG. 6 whereby closed circles refer to binding to p55-TNF-R-human IgGγ3- and open circles refer to binding to p75-TNF-R-human IgGγ3.

2. Determination of binding of Ser$^{29}$-Trp$^{32}$-TNFα, Gly$^{29}$-TNFα, Tyr$^{29}$-TNFα and Tyr$^{32}$-TNFα was performed as described under 1. with the only exception that MONO-Q ion exchange chromatography purified muteins were used. Results are shown in FIG. 7 whereby open and closed circles have the same meaning as in FIG. 6 and μg/ml gives the amount of purified mutein/ml.

---

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 157 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Homo sapiens
        ( F ) TISSUE TYPE: Blood
        ( G ) CELL TYPE: Macrophage ( x i ) SEQUENCE DESCRIPTION: SEQ ID NO:1:

```
Val  Arg  Ser  Ser  Ser  Arg  Thr  Pro  Ser  Asp  Lys  Pro  Val  Ala  His  Val
 1              5                          10                         15

Val  Ala  Asn  Pro  Gln  Ala  Glu  Gly  Gln  Leu  Gln  Trp  Leu  Asn  Arg  Arg
              20                          25                         30

Ala  Asn  Ala  Leu  Leu  Ala  Asn  Gly  Val  Glu  Leu  Arg  Asp  Asn  Gln  Leu
              35                          40                         45
```

```
            Val  Val  Pro  Ser  Glu  Gly  Leu  Tyr  Leu  Ile  Tyr  Ser  Gln  Val  Leu  Phe
             50                       55                       60

Lys  Gly  Gln  Gly  Cys  Pro  Ser  Thr  His  Val  Leu  Leu  Thr  His  Thr  Ile
             65                       70                       75                       80

Ser  Arg  Ile  Ala  Val  Ser  Tyr  Gln  Thr  Lys  Val  Asn  Leu  Leu  Ser  Ala
                                 85                       90                       95

Ile  Lys  Ser  Pro  Cys  Gln  Arg  Glu  Thr  Pro  Glu  Gly  Ala  Glu  Ala  Lys
                                100                      105                      110

Pro  Trp  Tyr  Glu  Pro  Ile  Tyr  Leu  Gly  Gly  Val  Phe  Gln  Leu  Glu  Lys
                           115                      120                      125

Gly  Asp  Arg  Leu  Ser  Ala  Glu  Ile  Asn  Arg  Pro  Asp  Tyr  Leu  Asp  Phe
                 130                      135                      140

Ala  Glu  Ser  Gly  Gln  Val  Tyr  Phe  Gly  Ile  Ile  Ala  Leu
             145                      150                      155
```

( 2 ) INFORMATION FOR SEQ ID NO:2:

( i ) SEQUENCE CHARACTERISTICS:
        ( A ) LENGTH: 3977 base pairs
        ( B ) TYPE: nucleic acid
        ( C ) STRANDEDNESS: single
        ( D ) TOPOLOGY: linear ( i i ) MOLECULE TYPE: DNA (recombinant plasmid)

( v i i ) IMMEDIATE SOURCE:
        ( B ) CLONE: pDS56/RBSII,Sph1-TNF- alpha ( i x ) FEATURE:
        ( A ) NAME/KEY: CDS
        ( B ) LOCATION: 115..591

( x i ) SEQUENCE DESCRIPTION: SEQ ID NO:2:

```
CTCGAGAAAT  CATAAAAAAT  TTATTTGCTT  TGTGAGCGGA  TAACAATTAT  AATAGATTCA          60

ATTGTGAGCG  ATAACAATT   TCACACAGGA  TTCATTAAAG  AGGAGAAATT  AAGC ATG          117
                                                                Met
                                                                  1

GTC  AGA  TCA  TCT  TCT  CGA  ACC  CCG  AGT  GAC  AAG  CCT  GTA  GCC  CAT  GTT    165
Val  Arg  Ser  Ser  Ser  Arg  Thr  Pro  Ser  Asp  Lys  Pro  Val  Ala  His  Val
                5                   10                      15

GTC  GCG  AAC  CCT  CAA  GCT  GAG  GGG  CAG  CTC  CAG  TGG  CTG  AAC  CGC  CGG    213
Val  Ala  Asn  Pro  Gln  Ala  Glu  Gly  Gln  Leu  Gln  Trp  Leu  Asn  Arg  Arg
           20                       25                       30

GCC  AAT  GCC  CTC  CTG  GCC  AAT  GGC  GTG  GAG  CTG  AGA  GAT  AAC  CAG  CTG    261
Ala  Asn  Ala  Leu  Leu  Ala  Asn  Gly  Val  Glu  Leu  Arg  Asp  Asn  Gln  Leu
      35                       40                       45

GTG  GTG  CCA  TCA  GAG  GGC  CTG  TAC  CTC  ATC  TAC  TCC  CAG  GTC  CTC  TTC    309
Val  Val  Pro  Ser  Glu  Gly  Leu  Tyr  Leu  Ile  Tyr  Ser  Gln  Val  Leu  Phe
 50                       55                       60                       65

AAG  GGC  CAA  GGC  TGC  CCC  TCC  ACC  CAT  GTG  CTC  CTC  ACC  CAC  ACC  ATC    357
Lys  Gly  Gln  Gly  Cys  Pro  Ser  Thr  His  Val  Leu  Leu  Thr  His  Thr  Ile
                     70                       75                       80

AGC  CGC  ATC  GCC  GTC  TCC  TAC  CAG  ACC  AAG  GTC  AAC  CTC  CTC  TCT  GCC    405
Ser  Arg  Ile  Ala  Val  Ser  Tyr  Gln  Thr  Lys  Val  Asn  Leu  Leu  Ser  Ala
                 85                       90                       95

ATC  AAG  AGC  CCC  TGC  CAG  AGG  GAG  ACC  CCA  GAG  GGG  GCT  GAG  GCC  AAG    453
Ile  Lys  Ser  Pro  Cys  Gln  Arg  Glu  Thr  Pro  Glu  Gly  Ala  Glu  Ala  Lys
                    100                      105                      110

CCC  TGG  TAT  GAG  CCC  ATC  TAT  CTG  GGA  GGG  GTC  TTC  CAG  CTG  GAG  AAG    501
Pro  Trp  Tyr  Glu  Pro  Ile  Tyr  Leu  Gly  Gly  Val  Phe  Gln  Leu  Glu  Lys
               115                      120                      125

GGT  GAC  CGA  CTC  AGC  GCT  GAG  ATC  AAT  CGG  CCC  GAC  TAT  CTC  GAC  TTT    549
Gly  Asp  Arg  Leu  Ser  Ala  Glu  Ile  Asn  Arg  Pro  Asp  Tyr  Leu  Asp  Phe
130                      135                      140                      145
```

-continued

| | | | | | | | | | | |
|---|---|---|---|---|---|---|---|---|---|---|
| GCC | GAG | TCT | GGG | CAG | GTC | TAC | TTT | GGG | ATC | ATT | GCC | CTG | TGAGGAGGAC | | 598 |
| Ala | Glu | Ser | Gly | Gln | Val | Tyr | Phe | Gly | Ile | Ile | Ala | Leu | | |
| | | | 150 | | | | | 155 | | | | | |

```
GAACATCCAA  CCTTCCCAAA  CGCCTCCCCT  GCCCCAATCC  CTTTATTACC  CCCTCCTTCA  658
GACACCCTCA  ACCTCTTCTG  GCTCAAAAAG  AGAATTGGGG  GCTTAGGGTC  GGAACCCAAG  718
CTTGGACTCC  TGTTGATAGA  TCCAGTAATG  ACCTCAGAAC  TCCATCTGGA  TTTGTTCAGA  778
ACGCTCGGTT  GCCGCCGGGG  GTTTTTTATT  GGTGAGAATC  CAAGCTAGCT  TGGCGAGATT  838
TTCAGGAGCT  AAGGAAGCTA  AAATGGAGAA  AAAAATCACT  GGATATACCA  CCGTTGATAT  898
ATCCCAATGG  CATCGTAAAG  AACATTTTGA  GGCATTTCAG  TCAGTTGCTC  AATGTACCTA  958
TAACCAGACC  GTTACGCTGG  ATATTACGGC  CTTTTTAAAG  ACCGTAAAGA  AAAATAAGCA  1018
CAAGTTTTAT  CCGGCCTTTA  TTCACATTCT  GCCCGCCTG   ATGAATGCTC  ATCCGGAATT  1078
TCGTATGGCA  ATGAAAGACG  GTGAGCTGGT  GATATGGGAT  AGTGTTCACC  CTTGTTACAC  1138
CGTTTTCCAT  GAGCAAACTG  AAACGTTTTC  ATCGCTCTGG  AGTGAATACC  ACGACGATTT  1198
CCGGCAGTTT  CTACACATAT  ATTCGCAAGA  TGTGGCGTGT  TACGGTGAAA  ACCTGGCCTA  1258
TTTCCCTAAA  GGGTTTATTG  AGAATATGTT  TTTCGTCTCA  GCCAATCCCT  GGGTGAGTTT  1318
CACCAGTTTT  GATTTAAACG  TGGCCAATAT  GGACAACTTC  TTCGCCCCCG  TTTTCACCAT  1378
GGGCAAATAT  TATACGCAAG  GCGACAAGGT  GCTGATGCCG  CTGGCGATTC  AGGTTCATCA  1438
TGCCGTCTGT  GATGGCTTCC  ATGTCGGCAG  AATGCTTAAT  GAATTACAAC  AGTACTGCGA  1498
TGAGTGGCAG  GGCGGGGCGT  AATTTTTTA   AGGCAGTTAT  TGGTGCCCTT  AAACGCCTGG  1558
GGTAATGACT  CTCTAGCTTG  AGGCATCAAA  TAAAACGAAA  GGCTCAGTCG  AAAGACTGGG  1618
CCTTTCGTTT  TATCTGTTGT  TTGTCGGTGA  ACGCTCTCCT  GAGTAGGACA  AATCCGCCGC  1678
TCTAGAGCTG  CCTCGCGCGT  TTCGGTGATG  ACGGTGAAAA  CCTCTGACAC  ATGCAGCTCC  1738
CGGAGACGGT  CACAGCTTGT  CTGTAAGCGG  ATGCCGGGAG  CAGACAAGCC  CGTCAGGGCG  1798
CGTCAGCGGG  TGTTGGCGGG  TGTCGGGGCG  CAGCCATGAC  CCAGTCACGT  AGCGATAGCG  1858
GAGTGTATAC  TGGCTTAACT  ATGCCGCATC  AGAGCAGATT  GTACTGAGAG  TGCACCATAT  1918
GCGGTGTGAA  ATACCGCACA  GATGCGTAAG  GAGAAAATAC  CGCATCAGGC  GCTCTTCCGC  1978
TTCCTCGCTC  ACTGACTCGC  TGCGCTCGGT  CTGTCGGCTG  CGGCGAGCGG  TATCAGCTCA  2038
CTCAAAGGCG  GTAATACGGT  TATCCACAGA  ATCAGGGGAT  AACGCAGGAA  AGAACATGTG  2098
AGCAAAAGGC  CAGCAAAAGG  CCAGGAACCG  TAAAAAGGCC  GCGTTGCTGG  CGTTTTTCCA  2158
TAGGCTCCGC  CCCCCTGACG  AGCATCACAA  AAATCGACGC  TCAAGTCAGA  GGTGGCGAAA  2218
CCCGACAGGA  CTATAAAGAT  ACCAGGCGTT  TCCCCCTGGA  AGCTCCCTCG  TGCGCTCTCC  2278
TGTTCCGACC  CTGCCGCTTA  CCGGATACCT  GTCCGCCTTT  CTCCCTTCGG  GAAGCGTGGC  2338
GCTTTCTCAA  TGCTCACGCT  GTAGGTATCT  CAGTTGCCTG  TAGGTCGTTC  GCTCCAAGCT  2398
GGGCTGTGTG  CACGAACCCC  CCGTTCAGCC  CGACCGCTGC  GCCTTATCCG  GTAACTATCG  2458
TCTTGAGTCC  AACCCGGTAA  GACACGACTT  ATCGCCACTG  GCAGCAGCCA  CTGGTAACAG  2518
GATTAGCAGA  GCGAGGTATG  TAGGGGGTGC  TACAGAGTTC  TTGAAGTGGT  GGCCTAACTA  2578
CGGCTACACT  AGAAGGACAG  TATTTGGTAT  CTGCGCTCTG  CTGAAGCCAG  TTACCTTCGG  2638
AAAAAGAGTT  GGTAGCTCTT  GATCCGGCAA  ACAAACCACC  GCTGGTAGCG  GTGGTTTTTT  2698
TGTTTGCAAG  CAGCAGATTA  CGCGCAGAAA  AAAAGGATCT  CAAGAAGATC  CTTTGATCTT  2758
TTCTACGGGG  TCTGACGCTC  AGTGGAACGA  AAACTCACGT  TAAGGGATTT  TGGTCATGAG  2818
ATTATCAAAA  AGGATCTTCA  CCTAGATCCT  TTTAAATTAA  AAATGAAGTT  TTAAATCAAT  2878
CTAAAGTATA  TATGAGTAAA  CTTGGTCTGA  CAGTTACCAA  TGCTTAATCA  GTGAGGCACC  2938
```

-continued

| | | | | | |
|---|---|---|---|---|---|
| TATCTCAGCG | ATCTGTCTAT | TTCGTTCATC | CATAGCTGCC | TGACTCCCCG | TCGTGTAGAT | 2998 |
| AACTACGATA | CGGGAGGGCT | TACCATCTGG | CCCCAGTGCT | GCAATGATAC | CGCGAGACCC | 3058 |
| ACGCTCACCG | GCTCCAGATT | TATCAGCAAT | AAACCAGCCA | GCCGGAAGGG | CCGAGCGCAG | 3118 |
| AAGTGGTCCT | GCAACTTTAT | CCGCCTCCAT | CCAGTCTATT | AATTGTTGCC | GGGAAGCTAG | 3178 |
| AGTAAGTAGT | CCGCCAGTTA | ATAGTTTGCG | CAACGTTGTT | GCCATTGCTA | CAGGCATCGT | 3238 |
| GGTCTCACGC | TCGTCGTTTG | GTATGGCTTC | ATTCAGCTCC | GGTTCCCAAC | GATCAAGGCG | 3298 |
| AGTTACATGA | TCCCCCATGT | TGTGCAAAAA | AGCGGTTAGC | TCCTTCGGTC | CTCCGATCGT | 3358 |
| TGTCAGAAGT | AAGTTGGCCG | CAGTGTTATC | ACTCATGGTT | ATGGCAGCAC | TGCATAATTC | 3418 |
| TCTTACTGTC | ATGCCATCCG | TAAGATGCTT | TTCTGTGACT | GGTGAGTACT | CAACCAAGTC | 3478 |
| ATTCTGAGAA | TAGTGTATGC | GGCGACCGAG | TTGCTCTTGC | CCGGCGTCAA | TACGGGATAA | 3538 |
| TACCGCGCCA | CATAGCAGAA | CTTTAAAAGT | GCTCATCATT | GGAAACGTT | CTTCGGGGCG | 3598 |
| AAAACTCTCA | AGGATCTTAC | CGCTGTTGAG | ATCCAGTTCG | ATGTAACCCA | CTCGTGCACC | 3658 |
| CAACTGATCT | TCAGCATCTT | TTACTTTCAC | CAGCGTTTCT | GGCTGAGCAA | AACAGGAAG | 3718 |
| GCAAAATGCC | GCAAAAAAGG | GAATAAGGGC | GACACGGAAA | TGTTGAATAC | TCATACTCTT | 3778 |
| CCTTTTTCAA | TATTATTGAA | GCATTTATCA | GGGTTATTGT | CTCATGAGCG | GATACATATT | 3838 |
| TGAATGTATT | TAGAAAAATA | AACAAATAGG | GGTTCCGCGC | ACATTTCCCC | GAAAAGTCCC | 3898 |
| ACCTGACGTC | TAAGAAACCA | TTATTATCAT | GACATTAACC | TATAAAAATA | GGCGTATCAC | 3958 |
| GAGGCCCTTT | CGTCTTCAC | | | | | 3977 |

( 2 ) INFORMATION FOR SEQ ID NO:3:

( i ) SEQUENCE CHARACTERISTICS:
        ( A ) LENGTH: 158 amino acids
        ( B ) TYPE: amino acid
        ( D ) TOPOLOGY: linear ( i i ) MOLECULE TYPE: protein ( i x ) FEATURE:
        ( A ) NAME/KEY: Modified site
        ( B ) LOCATION: 29, 31 and 32
        ( D ) OTHER INFORMATION:/note="Xaa =any naturally occurring amino acid"

( x i ) SEQUENCE DESCRIPTION: SEQ ID NO:3:

```
Met  Val  Arg  Ser  Ser  Ser  Arg  Thr  Pro  Ser  Asp  Lys  Pro  Val  Ala  His
 -1   +1             5                    10                       15

Val  Val  Ala  Asn  Pro  Gln  Ala  Glu  Gly  Gln  Leu  Gln  Trp  Xaa  Asn  Xaa
                20                   25                       30

Xaa  Ala  Asn  Ala  Leu  Leu  Ala  Asn  Gly  Val  Glu  Leu  Arg  Asp  Asn  Gln
               35                   40                       45

Leu  Val  Val  Pro  Ser  Glu  Gly  Leu  Tyr  Leu  Ile  Tyr  Ser  Gln  Val  Leu
          50                   55                       60

Phe  Lys  Gly  Gln  Gly  Cys  Pro  Ser  Thr  His  Val  Leu  Leu  Thr  His  Thr
     65                   70                       75

Ile  Ser  Arg  Ile  Ala  Val  Ser  Tyr  Gln  Thr  Lys  Val  Asn  Leu  Leu  Ser
 80                   85                   90                       95

Ala  Ile  Lys  Ser  Pro  Cys  Gln  Arg  Glu  Thr  Pro  Glu  Gly  Ala  Glu  Ala
               100                  105                      110

Lys  Pro  Trp  Tyr  Glu  Pro  Ile  Tyr  Leu  Gly  Gly  Val  Phe  Gln  Leu  Glu
               115                  120                      125

Lys  Gly  Asp  Arg  Leu  Ser  Ala  Glu  Ile  Asn  Arg  Pro  Asp  Tyr  Leu  Asp
          130                  135                      140
```

```
Phe Ala Glu Ser Gly Gln Val Tyr Phe Gly Ile Ile Ala Leu
145                 150                 155
```

(2) INFORMATION FOR SEQ ID NO:4:

(i) SEQUENCE CHARACTERISTICS:
    (A) LENGTH: 158 amino acids
    (B) TYPE: amino acid
    (D) TOPOLOGY: linear (ii) MOLECULE TYPE: protein (xi) SEQUENCE DESCRIPTION: SEQ ID NO:4:

```
Met Val Arg Ser Ser Ser Arg Thr Pro Ser Asp Lys Pro Val Ala His
 -1  +1              5                  10                  15

Val Val Ala Asn Pro Gln Ala Glu Gly Gln Leu Gln Trp Ser Asn Arg
             20                  25                  30

Arg Ala Asn Ala Leu Leu Ala Asn Gly Val Glu Leu Arg Asp Asn Gln
             35                  40                  45

Leu Val Val Pro Ser Glu Gly Leu Tyr Leu Ile Tyr Ser Gln Val Leu
             50                  55                  60

Phe Lys Gly Gln Gly Cys Pro Ser Thr His Val Leu Leu Thr His Thr
 65                  70                  75

Ile Ser Arg Ile Ala Val Ser Tyr Gln Thr Lys Val Asn Leu Leu Ser
 80                  85                  90                  95

Ala Ile Lys Ser Pro Cys Gln Arg Glu Thr Pro Glu Gly Ala Glu Ala
             100                 105                 110

Lys Pro Trp Tyr Glu Pro Ile Tyr Leu Gly Gly Val Phe Gln Leu Glu
             115                 120                 125

Lys Gly Asp Arg Leu Ser Ala Glu Ile Asn Arg Pro Asp Tyr Leu Asp
             130                 135                 140

Phe Ala Glu Ser Gly Gln Val Tyr Phe Gly Ile Ile Ala Leu
145                 150                 155
```

(2) INFORMATION FOR SEQ ID NO:5:

(i) SEQUENCE CHARACTERISTICS:
    (A) LENGTH: 158 amino acids
    (B) TYPE: amino acid
    (D) TOPOLOGY: linear (ii) MOLECULE TYPE: protein (xi) SEQUENCE DESCRIPTION: SEQ ID NO:5:

```
Met Val Arg Ser Ser Ser Arg Thr Pro Ser Asp Lys Pro Val Ala His
 -1  +1              5                  10                  15

Val Val Ala Asn Pro Gln Ala Glu Gly Gln Leu Gln Trp Gly Asn Arg
             20                  25                  30

Arg Ala Asn Ala Leu Leu Ala Asn Gly Val Glu Leu Arg Asp Asn Gln
             35                  40                  45

Leu Val Val Pro Ser Glu Gly Leu Tyr Leu Ile Tyr Ser Gln Val Leu
             50                  55                  60

Phe Lys Gly Gln Gly Cys Pro Ser Thr His Val Leu Leu Thr His Thr
 65                  70                  75

Ile Ser Arg Ile Ala Val Ser Tyr Gln Thr Lys Val Asn Leu Leu Ser
 80                  85                  90                  95

Ala Ile Lys Ser Pro Cys Gln Arg Glu Thr Pro Glu Gly Ala Glu Ala
             100                 105                 110

Lys Pro Trp Tyr Glu Pro Ile Tyr Leu Gly Gly Val Phe Gln Leu Glu
             115                 120                 125

Lys Gly Asp Arg Leu Ser Ala Glu Ile Asn Arg Pro Asp Tyr Leu Asp
```

|   |   | 130 |   |   | 135 |   |   | 140 |   |   |   |

Phe Ala Glu Ser Gly Gln Val Tyr Phe Gly Ile Ile Ala Leu
145                     150                 155

( 2 ) INFORMATION FOR SEQ ID NO:6:

( i ) SEQUENCE CHARACTERISTICS:
        ( A ) LENGTH: 158 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

Met Val Arg Ser Ser Ser Arg Thr Pro Ser Asp Lys Pro Val Ala His
-1  +1              5                   10                  15

Val Val Ala Asn Pro Gln Ala Glu Gly Gln Leu Gln Trp Tyr Asn Arg
            20              25                      30

Arg Ala Asn Ala Leu Leu Ala Asn Gly Val Glu Leu Arg Asp Asn Gln
            35              40                      45

Leu Val Val Pro Ser Glu Gly Leu Tyr Leu Ile Tyr Ser Gln Val Leu
        50              55                      60

Phe Lys Gly Gln Gly Cys Pro Ser Thr His Val Leu Leu Thr His Thr
    65              70                      75

Ile Ser Arg Ile Ala Val Ser Tyr Gln Thr Lys Val Asn Leu Leu Ser
80              85                      90                      95

Ala Ile Lys Ser Pro Cys Gln Arg Glu Thr Pro Glu Gly Ala Glu Ala
            100                     105                     110

Lys Pro Trp Tyr Glu Pro Ile Tyr Leu Gly Gly Val Phe Gln Leu Glu
            115                     120                     125

Lys Gly Asp Arg Leu Ser Ala Glu Ile Asn Arg Pro Asp Tyr Leu Asp
        130                     135                     140

Phe Ala Glu Ser Gly Gln Val Tyr Phe Gly Ile Ile Ala Leu
        145                     150                 155

( 2 ) INFORMATION FOR SEQ ID NO:7:

( i ) SEQUENCE CHARACTERISTICS:
        ( A ) LENGTH: 158 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

Met Val Arg Ser Ser Ser Arg Thr Pro Ser Asp Lys Pro Val Ala His
-1  +1              5                   10                  15

Val Val Ala Asn Pro Gln Ala Glu Gly Gln Leu Gln Trp Leu Asn Glu
            20              25                      30

Arg Ala Asn Ala Leu Leu Ala Asn Gly Val Glu Leu Arg Asp Asn Gln
            35              40                      45

Leu Val Val Pro Ser Glu Gly Leu Tyr Leu Ile Tyr Ser Gln Val Leu
        50              55                      60

Phe Lys Gly Gln Gly Cys Pro Ser Thr His Val Leu Leu Thr His Thr
    65              70                      75

Ile Ser Arg Ile Ala Val Ser Tyr Gln Thr Lys Val Asn Leu Leu Ser
80              85                      90                      95

Ala Ile Lys Ser Pro Cys Gln Arg Glu Thr Pro Glu Gly Ala Glu Ala
            100                     105                     110

Lys Pro Trp Tyr Glu Pro Ile Tyr Leu Gly Gly Val Phe Gln Leu Glu
            115                     120                     125

```
Lys Gly Asp Arg Leu Ser Ala Glu Ile Asn Arg Pro Asp Tyr Leu Asp
    130                 135                 140

Phe Ala Glu Ser Gly Gln Val Tyr Phe Gly Ile Ile Ala Leu
    145                 150                 155
```

(2) INFORMATION FOR SEQ ID NO:8:

(i) SEQUENCE CHARACTERISTICS:
        (A) LENGTH: 158 amino acids
        (B) TYPE: amino acid
        (D) TOPOLOGY: linear (ii) MOLECULE TYPE: protein (xi) SEQUENCE DESCRIPTION: SEQ ID NO:8:

```
Met Val Arg Ser Ser Ser Arg Thr Pro Ser Asp Lys Pro Val Ala His
 -1  +1          5                  10                      15

Val Val Ala Asn Pro Gln Ala Glu Gly Gln Leu Gln Trp Leu Asn Asn
            20                  25                  30

Arg Ala Asn Ala Leu Leu Ala Asn Gly Val Glu Leu Arg Asp Asn Gln
            35                  40                  45

Leu Val Val Pro Ser Glu Gly Leu Tyr Leu Ile Tyr Ser Gln Val Leu
        50                  55                  60

Phe Lys Gly Gln Gly Cys Pro Ser Thr His Val Leu Leu Thr His Thr
    65                  70                  75

Ile Ser Arg Ile Ala Val Ser Tyr Gln Thr Lys Val Asn Leu Leu Ser
 80                  85                  90                  95

Ala Ile Lys Ser Pro Cys Gln Arg Glu Thr Pro Glu Gly Ala Glu Ala
            100                 105                 110

Lys Pro Trp Tyr Glu Pro Ile Tyr Leu Gly Gly Val Phe Gln Leu Glu
            115                 120                 125

Lys Gly Asp Arg Leu Ser Ala Glu Ile Asn Arg Pro Asp Tyr Leu Asp
    130                 135                 140

Phe Ala Glu Ser Gly Gln Val Tyr Phe Gly Ile Ile Ala Leu
    145                 150                 155
```

(2) INFORMATION FOR SEQ ID NO:9:

(i) SEQUENCE CHARACTERISTICS:
        (A) LENGTH: 158 amino acids
        (B) TYPE: amino acid
        (D) TOPOLOGY: linear (ii) MOLECULE TYPE: protein (xi) SEQUENCE DESCRIPTION: SEQ ID NO:9:

```
Met Val Arg Ser Ser Ser Arg Thr Pro Ser Asp Lys Pro Val Ala His
 -1  +1          5                  10                      15

Val Val Ala Asn Pro Gln Ala Glu Gly Gln Leu Gln Trp Leu Asn Arg
            20                  25                  30

Trp Ala Asn Ala Leu Leu Ala Asn Gly Val Glu Leu Arg Asp Asn Gln
            35                  40                  45

Leu Val Val Pro Ser Glu Gly Leu Tyr Leu Ile Tyr Ser Gln Val Leu
        50                  55                  60

Phe Lys Gly Gln Gly Cys Pro Ser Thr His Val Leu Leu Thr His Thr
    65                  70                  75

Ile Ser Arg Ile Ala Val Ser Tyr Gln Thr Lys Val Asn Leu Leu Ser
 80                  85                  90                  95

Ala Ile Lys Ser Pro Cys Gln Arg Glu Thr Pro Glu Gly Ala Glu Ala
            100                 105                 110
```

```
Lys Pro Trp Tyr Glu Pro Ile Tyr Leu Gly Gly Val Phe Gln Leu Glu
            115                 120                 125

Lys Gly Asp Arg Leu Ser Ala Glu Ile Asn Arg Pro Asp Tyr Leu Asp
            130                 135                 140

Phe Ala Glu Ser Gly Gln Val Tyr Phe Gly Ile Ile Ala Leu
        145                 150                 155
```

( 2 ) INFORMATION FOR SEQ ID NO:10:

( i ) SEQUENCE CHARACTERISTICS:
        ( A ) LENGTH: 158 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Val Arg Ser Ser Ser Arg Thr Pro Ser Asp Lys Pro Val Ala His
 -1  +1              5                  10                  15

Val Val Ala Asn Pro Gln Ala Glu Gly Gln Leu Gln Trp Leu Asn Arg
             20                  25                  30

Tyr Ala Asn Ala Leu Leu Ala Asn Gly Val Glu Leu Arg Asp Asn Gln
             35                  40                  45

Leu Val Val Pro Ser Glu Gly Leu Tyr Leu Ile Tyr Ser Gln Val Leu
         50                  55                  60

Phe Lys Gly Gln Gly Cys Pro Ser Thr His Val Leu Leu Thr His Thr
        65                  70                  75

Ile Ser Arg Ile Ala Val Ser Tyr Gln Thr Lys Val Asn Leu Leu Ser
 80                  85                  90                  95

Ala Ile Lys Ser Pro Cys Gln Arg Glu Thr Pro Glu Gly Ala Glu Ala
            100                 105                 110

Lys Pro Trp Tyr Glu Pro Ile Tyr Leu Gly Gly Val Phe Gln Leu Glu
            115                 120                 125

Lys Gly Asp Arg Leu Ser Ala Glu Ile Asn Arg Pro Asp Tyr Leu Asp
            130                 135                 140

Phe Ala Glu Ser Gly Gln Val Tyr Phe Gly Ile Ile Ala Leu
        145                 150                 155
```

( 2 ) INFORMATION FOR SEQ ID NO:11:

( i ) SEQUENCE CHARACTERISTICS:
        ( A ) LENGTH: 158 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Met Val Arg Ser Ser Ser Arg Thr Pro Ser Asp Lys Pro Val Ala His
 -1  +1              5                  10                  15

Val Val Ala Asn Pro Gln Ala Glu Gly Gln Leu Gln Trp Leu Asn Asn
             20                  25                  30

Thr Ala Asn Ala Leu Leu Ala Asn Gly Val Glu Leu Arg Asp Asn Gln
             35                  40                  45

Leu Val Val Pro Ser Glu Gly Leu Tyr Leu Ile Tyr Ser Gln Val Leu
         50                  55                  60

Phe Lys Gly Gln Gly Cys Pro Ser Thr His Val Leu Leu Thr His Thr
        65                  70                  75

Ile Ser Arg Ile Ala Val Ser Tyr Gln Thr Lys Val Asn Leu Leu Ser
 80                  85                  90                  95

Ala Ile Lys Ser Pro Cys Gln Arg Glu Thr Pro Glu Gly Ala Glu Ala
```

|   |   |   |   |   | 100 |   |   |   |   | 105 |   |   |   |   | 110 |   |   |
|---|---|---|---|---|---|---|---|---|---|---|---|---|---|---|---|---|---|
| Lys | Pro | Trp | Tyr | Glu | Pro | Ile | Tyr | Leu | Gly | Gly | Val | Phe | Gln | Leu | Glu |
|   |   |   | 115 |   |   |   | 120 |   |   |   |   |   | 125 |   |   |
| Lys | Gly | Asp | Arg | Leu | Ser | Ala | Glu | Ile | Asn | Arg | Pro | Asp | Tyr | Leu | Asp |
|   |   | 130 |   |   |   | 135 |   |   |   |   | 140 |   |   |   |   |
| Phe | Ala | Glu | Ser | Gly | Gln | Val | Tyr | Phe | Gly | Ile | Ile | Ala | Leu |
|   | 145 |   |   |   | 150 |   |   |   |   | 155 |   |   |

( 2 ) INFORMATION FOR SEQ ID NO:12:

( i ) SEQUENCE CHARACTERISTICS:
        ( A ) LENGTH: 158 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| Met | Val | Arg | Ser | Ser | Ser | Arg | Thr | Pro | Ser | Asp | Lys | Pro | Val | Ala | His |
|---|---|---|---|---|---|---|---|---|---|---|---|---|---|---|---|
| -1 | +1 |   |   |   | 5 |   |   |   |   | 10 |   |   |   |   | 15 |
| Val | Val | Ala | Asn | Pro | Gln | Ala | Glu | Gly | Gln | Leu | Gln | Trp | Ser | Asn | Arg |
|   |   |   |   | 20 |   |   |   |   | 25 |   |   |   |   | 30 |   |
| Trp | Ala | Asn | Ala | Leu | Leu | Ala | Asn | Gly | Val | Glu | Leu | Arg | Asp | Asn | Gln |
|   |   |   | 35 |   |   |   |   | 40 |   |   |   |   | 45 |   |   |
| Leu | Val | Val | Pro | Ser | Glu | Gly | Leu | Tyr | Leu | Ile | Tyr | Ser | Gln | Val | Leu |
|   |   | 50 |   |   |   |   | 55 |   |   |   |   | 60 |   |   |   |
| Phe | Lys | Gly | Gln | Gly | Cys | Pro | Ser | Thr | His | Val | Leu | Leu | Thr | His | Thr |
|   | 65 |   |   |   |   | 70 |   |   |   |   | 75 |   |   |   |   |
| Ile | Ser | Arg | Ile | Ala | Val | Ser | Tyr | Gln | Thr | Lys | Val | Asn | Leu | Leu | Ser |
| 80 |   |   |   |   | 85 |   |   |   |   | 90 |   |   |   |   | 95 |
| Ala | Ile | Lys | Ser | Pro | Cys | Gln | Arg | Glu | Thr | Pro | Glu | Gly | Ala | Glu | Ala |
|   |   |   |   | 100 |   |   |   |   | 105 |   |   |   |   | 110 |   |
| Lys | Pro | Trp | Tyr | Glu | Pro | Ile | Tyr | Leu | Gly | Gly | Val | Phe | Gln | Leu | Glu |
|   |   |   | 115 |   |   |   | 120 |   |   |   |   |   | 125 |   |   |
| Lys | Gly | Asp | Arg | Leu | Ser | Ala | Glu | Ile | Asn | Arg | Pro | Asp | Tyr | Leu | Asp |
|   |   | 130 |   |   |   | 135 |   |   |   |   | 140 |   |   |   |   |
| Phe | Ala | Glu | Ser | Gly | Gln | Val | Tyr | Phe | Gly | Ile | Ile | Ala | Leu |
|   | 145 |   |   |   | 150 |   |   |   |   | 155 |   |   |

( 2 ) INFORMATION FOR SEQ ID NO:13:

( i ) SEQUENCE CHARACTERISTICS:
        ( A ) LENGTH: 3977 base pairs
        ( B ) TYPE: nucleic acid
        ( C ) STRANDEDNESS: single
        ( D ) TOPOLOGY: linear ( i i ) MOLECULE TYPE: DNA (recombinant plasmid)

( v i i ) IMMEDIATE SOURCE:
        ( B ) CLONE: pDS56/RBSII,Sph1-TNF- alpha ( i x ) FEATURE:
        ( A ) NAME/KEY: CDS
        ( B ) LOCATION: 115..591

( i x ) FEATURE:
        ( A ) NAME/KEY: Modified site
        ( B ) LOCATION: 202-204, 208-210 and 211-213
        ( D ) OTHER INFORMATION:/note="N =A, G, C or T"

( x i ) SEQUENCE DESCRIPTION: SEQ ID NO:13:

```
CTCGAGAAAT CATAAAAAAT TTATTTGCTT TGTGAGCGGA TAACAATTAT AATAGATTCA      60

ATTGTGAGCG GATAACAATT TCACACAGGA TTCATTAAAG AGGAGAAATT AAGC ATG       117
                                                            Met
```

-continued

| | | | | | | | | | | | | | | | |
|---|---|---|---|---|---|---|---|---|---|---|---|---|---|---|---|
| GTC | AGA | TCA | TCT | TCT | CGA | ACC | CCG | AGT | GAC | AAG | CCT | GTA | GCC | CAT | GTT | 165 |
| Val | Arg | Ser | Ser | Ser | Arg | Thr | Pro | Ser | Asp | Lys | Pro | Val | Ala | His | Val | |
| +1 | | | 5 | | | | | 10 | | | | | | 15 | | |
| GTC | GCG | AAC | CCT | CAA | GCT | GAG | GGG | CAG | CTC | CAG | TGG | NNN | AAC | NNN | NNN | 213 |
| Val | Ala | Asn | Pro | Gln | Ala | Glu | Gly | Gln | Leu | Gln | Trp | Xaa | Asn | Xaa | Xaa | |
| | | | 20 | | | | | 25 | | | | | 30 | | | |
| GCC | AAT | GCC | CTC | CTG | GCC | AAT | GGC | GTG | GAG | CTG | AGA | GAT | AAC | CAG | CTG | 261 |
| Ala | Asn | Ala | Leu | Leu | Ala | Asn | Gly | Val | Glu | Leu | Arg | Asp | Asn | Gln | Leu | |
| | | 35 | | | | | 40 | | | | | 45 | | | | |
| GTG | GTG | CCA | TCA | GAG | GGC | CTG | TAC | CTC | ATC | TAC | TCC | CAG | GTC | CTC | TTC | 309 |
| Val | Val | Pro | Ser | Glu | Gly | Leu | Tyr | Leu | Ile | Tyr | Ser | Gln | Val | Leu | Phe | |
| | 50 | | | | | 55 | | | | | 60 | | | | | |
| AAG | GGC | CAA | GGC | TGC | CCC | TCC | ACC | CAT | GTG | CTC | CTC | ACC | CAC | ACC | ATC | 357 |
| Lys | Gly | Gln | Gly | Cys | Pro | Ser | Thr | His | Val | Leu | Leu | Thr | His | Thr | Ile | |
| 65 | | | | | 70 | | | | | 75 | | | | | 80 | |
| AGC | CGC | ATC | GCC | GTC | TCC | TAC | CAG | ACC | AAG | GTC | AAC | CTC | CTC | TCT | GCC | 405 |
| Ser | Arg | Ile | Ala | Val | Ser | Tyr | Gln | Thr | Lys | Val | Asn | Leu | Leu | Ser | Ala | |
| | | | | 85 | | | | | 90 | | | | | 95 | | |
| ATC | AAG | AGC | CCC | TGC | CAG | AGG | GAG | ACC | CCA | GAG | GGG | GCT | GAG | GCC | AAG | 453 |
| Ile | Lys | Ser | Pro | Cys | Gln | Arg | Glu | Thr | Pro | Glu | Gly | Ala | Glu | Ala | Lys | |
| | | | 100 | | | | | 105 | | | | | 110 | | | |
| CCC | TGG | TAT | GAG | CCC | ATC | TAT | CTG | GGA | GGG | GTC | TTC | CAG | CTG | GAG | AAG | 501 |
| Pro | Trp | Tyr | Glu | Pro | Ile | Tyr | Leu | Gly | Gly | Val | Phe | Gln | Leu | Glu | Lys | |
| | | 115 | | | | | 120 | | | | | 125 | | | | |
| GGT | GAC | CGA | CTC | AGC | GCT | GAG | ATC | AAT | CGG | CCC | GAC | TAT | CTC | GAC | TTT | 549 |
| Gly | Asp | Arg | Leu | Ser | Ala | Glu | Ile | Asn | Arg | Pro | Asp | Tyr | Leu | Asp | Phe | |
| | 130 | | | | | 135 | | | | | 140 | | | | | |
| GCC | GAG | TCT | GGG | CAG | GTC | TAC | TTT | GGG | ATC | ATT | GCC | CTG | TGAGGAGGAC | | | 598 |
| Ala | Glu | Ser | Gly | Gln | Val | Tyr | Phe | Gly | Ile | Ile | Ala | Leu | | | | |
| 145 | | | | 150 | | | | | 155 | | | | | | | |

```
GAACATCCAA CCTTCCCAAA CGCCTCCCCT GCCCCAATCC CTTTATTACC CCCTCCTTCA      658
GACACCCTCA ACCTCTTCTG GCTCAAAAAG AGAATTGGGG CTTAGGGTC  GGAACCCAAG     718
CTTGGACTCC TGTTGATAGA TCCAGTAATG ACCTCAGAAC TCCATCTGGA TTTGTTCAGA     778
ACGCTCGGTT GCCGCCGGGG GTTTTTATT  GGTGAGAATC CAAGCTAGCT TGGCGAGATT     838
TTCAGGAGCT AAGGAAGCTA AATGGAGAA  AAAAATCACT GGATATACCA CCGTTGATAT     898
ATCCCAATGG CATCGTAAAG AACATTTTGA GGCATTTCAG TCAGTTGCTC AATGTACCTA     958
TAACCAGACC GTTACGCTGG ATATTACGGC CTTTTTAAAG ACCGTAAAGA AAAATAAGCA    1018
CAAGTTTTAT CCGGCCTTTA TTCACATTCT TGCCCGCCTG ATGAATGCTC ATCCGGAATT    1078
TCGTATGGCA ATGAAAGACG GTGAGCTGGT GATATGGGAT AGTGTTCACC CTTGTTACAC    1138
CGTTTTCCAT GAGCAAACTG AAACGTTTTC ATCGCTCTGG AGTGAATACC ACGACGATTT    1198
CCGGCAGTTT CTACACATAT ATTCGCAAGA TGTGGCGTGT TACGGTGAAA ACCTGGCCTA    1258
TTTCCCTAAA GGGTTTATTG AGAATATGTT TTTCGTCTCA GCCAATCCCT GGGTGAGTTT    1318
CACCAGTTTT GATTTAAACG TGGCCAATAT GGACAACTTC TTCGCCCCCG TTTTCACCAT    1378
GGGCAAATAT TATACGCAAG GCGACAAGGT GCTGATGCCG CTGGCGATTC AGGTTCATCA    1438
TGCCGTCTGT GATGGCTTCC ATGTCGGCAG AATGCTTAAT GAATTACAAC AGTACTGCGA    1498
TGAGTGGCAG GGCGGGGCGT AATTTTTTTA AGGCAGTTAT TGGTGCCCTT AAACGCCTGG    1558
GGTAATGACT CTCTAGCTTG AGGCATCAAA TAAAACGAAA GGCTCAGTCG AAAGACTGGG    1618
CCTTTCGTTT TATCTGTTGT TTGTCGGTGA ACGCTCTCCT GAGTAGGACA AATCCGCCGC    1678
TCTAGAGCTG CCTCGCGCGT TTCGGTGATG ACGGTGAAAA CCTCTGACAC ATGCAGCTCC    1738
CGGAGACGGT CACAGCTTGT CTGTAAGCGG ATGCCGGGAG CAGACAAGCC CGTCAGGGCG    1798
```

```
CGTCAGCGGG TGTTGGCGGG TGTCGGGGCG CAGCCATGAC CCAGTCACGT AGCGATAGCG    1858
GAGTGTATAC TGGCTTAACT ATGCCGCATC AGAGCAGATT GTACTGAGAG TGCACCATAT    1918
GCGGTGTGAA ATACCGCACA GATGCGTAAG GAGAAAATAC CGCATCAGGC GCTCTTCCGC    1978
TTCCTCGCTC ACTGACTCGC TGCGCTCGGT CTGTCGGCTG CGGCGAGCGG TATCAGCTCA    2038
CTCAAAGGCG GTAATACGGT TATCCACAGA ATCAGGGGAT AACGCAGGAA AGAACATGTG    2098
AGCAAAAGGC CAGCAAAAGG CCAGGAACCG TAAAAAGGCC GCGTTGCTGG CGTTTTTCCA    2158
TAGGCTCCGC CCCCCTGACG AGCATCACAA AAATCGACGC TCAAGTCAGA GGTGGCGAAA    2218
CCCGACAGGA CTATAAAGAT ACCAGGCGTT TCCCCCTGGA AGCTCCCTCG TGCGCTCTCC    2278
TGTTCCGACC CTGCCGCTTA CCGGATACCT GTCCGCCTTT CTCCCTTCGG AAGCGTGGC    2338
GCTTTCTCAA TGCTCACGCT GTAGGTATCT CAGTTGCCTG TAGGTCGTTC GCTCCAAGCT    2398
GGGCTGTGTG CACGAACCCC CCGTTCAGCC CGACCGCTGC GCCTTATCCG GTAACTATCG    2458
TCTTGAGTCC AACCCGGTAA GACACGACTT ATCGCCACTG GCAGCAGCCA CTGGTAACAG    2518
GATTAGCAGA GCGAGGTATG TAGGGGGTGC TACAGAGTTC TTGAAGTGGT GGCCTAACTA    2578
CGGCTACACT AGAAGGACAG TATTTGGTAT CTGCGCTCTG CTGAAGCCAG TTACCTTCGG    2638
AAAAAGAGTT GGTAGCTCTT GATCCGGCAA ACAAACCACC GCTGGTAGCG GTGGTTTTTT    2698
TGTTTGCAAG CAGCAGATTA CGCGCAGAAA AAAAGGATCT CAAGAAGATC CTTTGATCTT    2758
TTCTACGGGG TCTGACGCTC AGTGGAACGA AAACTCACGT TAAGGGATTT TGGTCATGAG    2818
ATTATCAAAA AGGATCTTCA CCTAGATCCT TTTAAATTAA AAATGAAGTT TTAAATCAAT    2878
CTAAAGTATA TATGAGTAAA CTTGGTCTGA CAGTTACCAA TGCTTAATCA GTGAGGCACC    2938
TATCTCAGCG ATCTGTCTAT TTCGTTCATC CATAGCTGCC TGACTCCCCG TCGTGTAGAT    2998
AACTACGATA CGGGAGGGCT TACCATCTGG CCCCAGTGCT GCAATGATAC CGCGAGACCC    3058
ACGCTCACCG GCTCCAGATT TATCAGCAAT AAACCAGCCA GCCGGAAGGG CCGAGCGCAG    3118
AAGTGGTCCT GCAACTTTAT CCGCCTCCAT CCAGTCTATT AATTGTTGCC GGGAAGCTAG    3178
AGTAAGTAGT CCGCCAGTTA ATAGTTTGCG CAACGTTGTT GCCATTGCTA CAGGCATCGT    3238
GGTCTCACGC TCGTCGTTTG GTATGGCTTC ATTCAGCTCC GGTTCCCAAC GATCAAGGCG    3298
AGTTACATGA TCCCCCATGT TGTGCAAAAA AGCGGTTAGC TCCTTCGGTC CTCCGATCGT    3358
TGTCAGAAGT AAGTTGGCCG CAGTGTTATC ACTCATGGTT ATGGCAGCAC TGCATAATTC    3418
TCTTACTGTC ATGCCATCCG TAAGATGCTT TTCTGTGACT GGTGAGTACT CAACCAAGTC    3478
ATTCTGAGAA TAGTGTATGC GGCGACCGAG TTGCTCTTGC CCGGCGTCAA TACGGGATAA    3538
TACCGCGCCA CATAGCAGAA CTTTAAAAGT GCTCATCATT GGAAAACGTT CTTCGGGGCG    3598
AAAACTCTCA AGGATCTTAC CGCTGTTGAG ATCCAGTTCG ATGTAACCCA CTCGTGCACC    3658
CAACTGATCT TCAGCATCTT TTACTTTCAC CAGCGTTTCT GGCTGAGCAA AAACAGGAAG    3718
GCAAAATGCC GCAAAAAAGG GAATAAGGGC GACACGGAAA TGTTGAATAC TCATACTCTT    3778
CCTTTTTCAA TATTATTGAA GCATTTATCA GGGTTATTGT CTCATGAGCG GATACATATT    3838
TGAATGTATT TAGAAAAATA AACAAATAGG GGTTCCGCGC ACATTTCCCC GAAAAGTCCC    3898
ACCTGACGTC TAAGAAACCA TTATTATCAT GACATTAACC TATAAAAATA GGCGTATCAC    3958
GAGGCCCTTT CGTCTTCAC                                                 3977
```

( 2 ) INFORMATION FOR SEQ ID NO:14:

( i ) SEQUENCE CHARACTERISTICS:
        ( A ) LENGTH: 3740 base pairs
        ( B ) TYPE: nucleic acid
        ( C ) STRANDEDNESS: single
        ( D ) TOPOLOGY: linear 5,422,104

-continued ( i i ) MOLECULE TYPE: DNA (recombinant plasmid)

( i x ) FEATURE:
    ( A ) NAME/KEY: CDS
    ( B ) LOCATION: complement (2613..one- of(1532))
    ( D ) OTHER INFORMATION: /note="Contains coding region for
        the lacI gene beginning at residue 2613 to 1532"

( x i ) SEQUENCE DESCRIPTION: SEQ ID NO:14:

| | | | | | | |
|---|---|---|---|---|---|---|
| AAGCTTCACG | CTGCCGCAAG | CACTCAGGGC | GCAAGGGCTG | CTAAAGGAAG | CGGAACACGT | 60 |
| AGAAAGCCAG | TCCGCAGAAA | CGGTGCTGAC | CCCGGATGAA | TGTCAGCTAC | TGGGCTATCT | 120 |
| GGACAAGGGA | AAACGCAAGC | GCAAAGAGAA | AGCAGGTAGC | TTGCAGTGGG | CTTACATGGC | 180 |
| GATAGCTAGA | CTGGGCGGTT | TTATGGACAG | CAAGCGAACC | GGAATTGCCA | GCTGGGGCGC | 240 |
| CCTCTGGTAA | CGTTGGGAAG | CCCTGCAAAG | TAAACTGGAT | GGCTTTCTTG | CCGCCAAGGA | 300 |
| TCTGATGGCG | CAGGGGATCA | AGATCTGATC | AAGAGACAGG | ATGACGGTCG | TTTCGCATGC | 360 |
| TTGAACAAGA | TGGATTGCAC | GCAGGTTCTC | CGGCCGCTTG | GGTCGAGAGG | CTATTCGGCT | 420 |
| ATGACTGGGC | ACAACAGACA | ATCCGCTGCT | CTGATGCCGC | CGTGTTCCGG | CTGTCAGCCC | 480 |
| AGGGGCGCCC | GGTTCTTTTT | GTCAAGACCG | ACCTGTCCGG | TGCCCTGAAT | GAACTGCAGG | 540 |
| ACGAGGCAGC | GCGGCTATCG | TGGCTGGCCA | CGACGGGCGT | TCCTTGCGCA | GCTGTGCTCG | 600 |
| ACGTTGTCAC | TGAAGCGGGA | AGGGACTGGC | TGCTATTGGG | CGAAGTGCCG | GGGCAGGATC | 660 |
| TCCTGTCATC | TCACCTTGCT | CCTGCCGAGA | AAGTATCCAT | CATGGCTGAT | GCAATGCGGC | 720 |
| GGCTGCATAC | GCTTGATCCG | GCTACCTGCC | CATTCGACCA | CCAAGCGAAA | CATCGCATCG | 780 |
| AGCGAGCACG | TACTCGGATG | GAAGCCGGTC | TTGTCGATCA | GGATCATCTG | GACGAAGAGC | 840 |
| ATCAGGGGCT | CGCGCCAGCC | GAACTGTTCG | CCAGGCTCAA | GGCGCGCATG | CCCGACGGCG | 900 |
| AGGATCTCGT | CGTGACCCAT | GGCGATGCCT | GCTTGCCGAA | TATCATGGTG | GAAAATGGCC | 960 |
| GCTTTTCTGG | ATTCATCGAC | TGTGGCCGGC | TGGGTGTGGC | GGACCGCTAT | CAGGACATAG | 1020 |
| CGTTGGCTAC | CCGTGATATT | GCTGAAGAGC | TTGGCGGCGA | ATGGGCTGAC | CGCTTCCTCG | 1080 |
| TGCTTTACGG | TATCGCCGCT | CCCGATTCGC | AGCGCATCGC | CTTCTATCGC | CTTCTTGACG | 1140 |
| AGTTCTTCTG | AGCGGGACTC | TGGGGTTCGA | AATGACCGAC | CAAGCGACGC | CCAACCTGCC | 1200 |
| ATCACGAGAT | TTCGATTCCA | CCGCCGCCTT | CTATGAAAGG | TTGGGCTTCG | GAATCGTTTT | 1260 |
| CCGGGACGCC | GGCTGGATGA | TCCTCCAGCG | CGGGGATCTC | ATGCTGGAGT | TCTTCGCCCA | 1320 |
| CCCCGGGCTC | GATCCCCTCG | CGAGTTGGTT | CAGCTGCTGC | CTGAGGCTGG | ACGACCTCGC | 1380 |
| GGAGTTCTAC | CGGCAGTGCA | AATCCGTCGG | CATCCAGGAA | ACCAGCAGCG | GCTATCCGCG | 1440 |
| CATCCATGCC | CCCGAACTGC | AGGAGTGGGG | AGGCACGATG | GCCGCTTTGG | TCGACAATTC | 1500 |
| GCGCTAACTT | ACATTAATTG | CGTTGCGCTC | ACTGCCCGCT | TTCCAGTCGG | GAAACCTGTC | 1560 |
| GTGCCAGCTG | CATTAATGAA | TCGGCCAACG | CGCGGGGAGA | GGCGGTTTGC | GTATTGGGCG | 1620 |
| CCAGGGTGGT | TTTTCTTTTC | ACCAGTGAGA | CGGGCAACAG | CTGATTGCCC | TTCACCGCCT | 1680 |
| GGCCCTGAGA | GAGTTGCAGC | AAGCGGTCCA | CGCTGGTTTG | CCCCAGCAGG | CGAAAATCCT | 1740 |
| GTTTGATGGT | GGTTAACGGC | GGGATATAAC | ATGAGCTGTC | TTCGGTATCG | TCGTATCCCA | 1800 |
| CTACCGAGAT | ATCCGCACCA | ACGCGCAGCC | CGGACTCGGT | AATGGCGCGC | ATTGCGCCCA | 1860 |
| GCGCCATCTG | ATCGTTGGCA | ACCAGCATCG | CAGTGGGAAC | GATGCCCTCA | TTCAGCATTT | 1920 |
| GCATGGTTTG | TTGAAAACCG | GACATGGCAC | TCCAGTCGCC | TTCCCGTTCC | GCTATCGGCT | 1980 |
| GAATTTGATT | GCGAGTGAGA | TATTTATGCC | AGCCAGCCAG | ACGCAGACGC | GCCGAGACAG | 2040 |
| AACTTAATGG | GCCCGCTAAC | AGCGCGATTT | GCTGGTGACC | CAATGCGACC | AGATGCTCCA | 2100 |
| CGCCCAGTCG | CGTACCGTCT | TCATGGGAGA | AAATAATACT | GTTGATGGGT | GTCTGGTCAG | 2160 |

| | | | | | |
|---|---|---|---|---|---|
| AGACATCAAG | AAATAACGCC | GGAACATTAG | TGCAGGCAGC | TTCCACAGCA | ATGGCATCCT | 2220
| GGTCATCCAG | CGGATAGTTA | ATGATCAGCC | CACTGACGCG | TTGCGCGAGA | AGATTGTGCA | 2280
| CCGCCGCTTT | ACAGGCTTCG | ACGCCGCTTC | GTTCTACCAT | CGACACCACC | ACGCTGGCAC | 2340
| CCAGTTGATC | GGCGCGAGAT | TTAATCGCCG | CGACAATTTG | CGACGGCGCG | TGCAGGGCCA | 2400
| GACTGGAGGT | GGCAACGCCA | ATCAGCAACG | ACTGTTTGCC | CGCCAGTTGT | TGTGCCACGC | 2460
| GGTTGGGAAT | GTAATTCAGC | TCCCCCATCG | CCGCTTCCAC | TTTTCCCGC | GTTTTCGCAG | 2520
| AAACGTGGCT | GGCCTGGTTC | ACCACGCGGG | AAACGGTCTG | ATAAGAGACA | CCGGCATACT | 2580
| CTGCGACATC | GTATAACGTT | ACTGGTTTCA | CATTCACCAC | CCTGAATTGA | CTCTCTTCCG | 2640
| GGCGCTATCA | TGCCATACCG | CGAAAGGTTT | TGCGCCATTC | GATGGTGTCA | ACGTAAATGC | 2700
| ATGCCGCTTC | GCCTTCGCCC | GCGAATTGTC | GACCCTGTCC | CTCCTGTTCA | GCTACTGACG | 2760
| GGGTGGTGCG | TAACGGCAAA | AGCACCGCCG | GACATCAGCG | CTAGCGGAGT | GTATACTGGC | 2820
| TTACTATGTT | GGCACTGATG | AGGGTGTCAG | TGAAGTGCTT | CATGTGGCAG | GAGAAAAAG | 2880
| GCTGCACCGG | TGCGTCAGCA | GAATATGTGA | TACAGGATAT | ATTCCGCTTC | CTCGCTCACT | 2940
| GACTCGCTAC | GCTCGGTCGT | TCGACTGCGG | CGAGCGGAAA | TGGCTTACGA | ACGGGCGGA | 3000
| GATTTCCTGG | AAGATGCCAG | GAAGATACTT | AACAGGGAAG | TGAGAGGGCC | GCGGCAAAGC | 3060
| CGTTTTCCA | TAGGCTCCGC | CCCCCTGACA | AGCATCACGA | AATCTGACGC | TCAAATCAGT | 3120
| GGTGGCGAAA | CCCCACAGGA | CTATAAAGAT | ACCAGGCGTT | TCCCTGGCG | GCTCCCTCGT | 3180
| GCGCTCTCCT | GTTCCTGCCT | TTCCGTTTAC | CGGTGTCATT | CCGCTGTTAT | GGCCGCGTTT | 3240
| GTCTCATTCC | ACGCCTGACA | CTCAGTTCCG | GGTAGGCAGT | TCGCTCCAAG | CTGGACTGTA | 3300
| TGCACGAACC | CCCCGTTCAG | TCCGACCGCT | GCGCCTTATC | CGGTAACTAT | CGTCTTGAGT | 3360
| CCAACCCGGA | AAGACATGCA | AAAGCACCAC | TGGCAGCAGC | CACTGGTAAT | TGATTTAGAG | 3420
| GAGTTAGTCT | TGAAGTCATG | CGCCGGTTAA | GGCTAAACTG | AAAGGACAAG | TTTTCGTCAC | 3480
| TGCGCTCCTC | CAAGCCAGTT | ACCTCGGTTC | AAAGAGTTGG | TAGCTCAGAG | AACCTTCGAA | 3540
| AAACCGCCCT | GCAAGGCGGT | TTTTTCGTTT | TCAGAGCAAG | AGATTACGCG | CAGACCAAAA | 3600
| CGATCTCAAG | AAGATCATCT | TATTAATCAG | ATAAAATATT | TCTAGATTTC | AGTGCAATTT | 3660
| ATCTCTTCAA | ATGTAGCACC | TGAAGTCAGC | CCCATACGAT | ATAAGTTGTT | AATTCTCATG | 3720
| TTTGACAGCT | TATCATCGAT | | | | | 3740

( 2 ) INFORMATION FOR SEQ ID NO:15:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( i x ) FEATURE:
        ( A ) NAME/KEY: misc_feature
        ( B ) LOCATION: 1..22
        ( D ) OTHER INFORMATION: /function=
          "Oligonucleotide used for gap
          duplex mutagenesis"

( x i ) SEQUENCE DESCRIPTION: SEQ ID NO:15:

CCGGCGGTTG GACCACTGGA GC                    22

( 2 ) INFORMATION FOR SEQ ID NO:16:

( i ) SEQUENCE CHARACTERISTICS:
        ( A ) LENGTH: 19 base pairs (B) TYPE: nucleic acid
(C) STRANDEDNESS: single
(D) TOPOLOGY: linear (i i) MOLECULE TYPE: DNA (oligonucleotide)

(i x) FEATURE:
(A) NAME/KEY: misc_feature
(B) LOCATION: 1..19
(D) OTHER INFORMATION: /function=
" Oligonucleotide used for gap
duplex mutagenesis"

(x i) SEQUENCE DESCRIPTION: SEQ ID NO:16:

CATTGGCCCA GCGGTTCAG  19

(2) INFORMATION FOR SEQ ID NO:17:

(i) SEQUENCE CHARACTERISTICS:
(A) LENGTH: 32 base pairs
(B) TYPE: nucleic acid
(C) STRANDEDNESS: single
(D) TOPOLOGY: linear (i i) MOLECULE TYPE: DNA (oligonucleotide)

(i x) FEATURE:
(A) NAME/KEY: misc_feature
(B) LOCATION: 1..32
(D) OTHER INFORMATION: /function=
" Oligonucleotide used for gap
duplex mutagenesis"

(x i) SEQUENCE DESCRIPTION: SEQ ID NO:17:

GGGCATTGGC CCAGCGGTTG GACCACTGGA GC  32

(2) INFORMATION FOR SEQ ID NO:18:

(i) SEQUENCE CHARACTERISTICS:
(A) LENGTH: 50 base pairs
(B) TYPE: nucleic acid
(C) STRANDEDNESS: single
(D) TOPOLOGY: linear (i i) MOLECULE TYPE: DNA (oligonucleotide)

(i x) FEATURE:
(A) NAME/KEY: misc_feature
(B) LOCATION: 1..50
(D) OTHER INFORMATION: /function=
" Oligonucleotide used for gap
duplex mutagenesis"
/ note="Used to create any position 29-mutein of
TNF-alpha"

(x i) SEQUENCE DESCRIPTION: SEQ ID NO:18:

CCACGCCATT CGCGAGGAGG GCATTGGCCC GGCGGTTNNN CCACTGGAGC  50

(2) INFORMATION FOR SEQ ID NO:19:

(i) SEQUENCE CHARACTERISTICS:
(A) LENGTH: 42 base pairs
(B) TYPE: nucleic acid
(C) STRANDEDNESS: single
(D) TOPOLOGY: linear (i i) MOLECULE TYPE: DNA (oligonucleotide)

(i x) FEATURE:
(A) NAME/KEY: misc_feature
(B) LOCATION: 1..42
(D) OTHER INFORMATION: /function=
" Oligonucleotide used for gap
duplex mutagenesis"
/ note="Used to create any position 32-mutein of
TNF-alpha"

( x i ) SEQUENCE DESCRIPTION: SEQ ID NO:19:

CCACGCCATT CGCGAGGAGG GCATTGGCNN NGCGGTTCAG CC    42

( 2 ) INFORMATION FOR SEQ ID NO:20:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( i x ) FEATURE:
        ( A ) NAME/KEY: misc_feature
        ( B ) LOCATION: complement (1..22)
        ( D ) OTHER INFORMATION: /function="PCR primer"
            / note="Complementary to positions 3949 to 3970 of
            Sequence ID No. 2"

( x i ) SEQUENCE DESCRIPTION: SEQ ID NO:20:

GGCGTATCAC GAGGCCCTTT CG    22

( 2 ) INFORMATION FOR SEQ ID NO:21:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( i x ) FEATURE:
        ( A ) NAME/KEY: misc_feature
        ( B ) LOCATION: 1..22
        ( D ) OTHER INFORMATION: /function="PCR primer"
            / note="Complementary to positions
            748 - 727 of Seq. ID No. 2"

( x i ) SEQUENCE DESCRIPTION: SEQ ID NO:21:

CATTACTGGA TCTATCAACA GG    22

( 2 ) INFORMATION FOR SEQ ID NO:22:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( i x ) FEATURE:
        ( A ) NAME/KEY: misc_feature
        ( B ) LOCATION: 1..36
        ( D ) OTHER INFORMATION: /function="PCR primer"
            / product="primer 21/M5"
            / note="PCR primer which is complementary to
            positions 219-184 of Seq. ID No. 2 with mismatched
            residues at positions 10-12."

( x i ) SEQUENCE DESCRIPTION: SEQ ID NO:22:

ATTGGCCCGC TCGTTCAGCC ACTGGAGCTG CCCCTC    36

( 2 ) INFORMATION FOR SEQ ID NO:23:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear (i i) MOLECULE TYPE: DNA (oligonucleotide)

(i x) FEATURE:
    (A) NAME/KEY: misc_feature
    (B) LOCATION: 1..36
    (D) OTHER INFORMATION: /function="PCR primer for mutagenesis"
    / note="PCR primer for mutagenesis which is complementary to positions 219-184 of Seq. ID No. 2 with mismatched bases at positions 7-9 and 11-12

(x i) SEQUENCE DESCRIPTION: SEQ ID NO:23:

ATTGGCAGTG TTGTTCAGCC ACTGGAGCTG CCCCTC    36

(2) INFORMATION FOR SEQ ID NO:24:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (i i) MOLECULE TYPE: DNA (oligonucleotide)

(i x) FEATURE:
    (A) NAME/KEY: misc_feature
    (B) LOCATION: 1..22
    (D) OTHER INFORMATION: /function="PCR primer"
    / product="primer 21/MR"
    / note="PCR primer used in conjunction with Seq. ID Nos. 22 & 23 to create muteins of TNF-alpha"

(x i) SEQUENCE DESCRIPTION: SEQ ID NO:24:

GCCCTCCTGG CCAATGGCGT GG    22

We claim:

1. A human Tumor Necrosis Factor mutein or a pharmaceutically acceptable salt thereof consisting of SEQ ID NO:4.

2. A human Tumor Necrosis Factor mutein or a pharmaceutically acceptable salt thereof consisting of SEQ ID NO: 5.

3. A human Tumor Necrosis Factor mutein or a pharmaceutically acceptable salt thereof consisting of SEQ ID NO: 6.

4. A human Tumor Necrosis Factor mutein or a pharmaceutically acceptable salt thereof consisting of SEQ ID NO: 12.

* * * * *